US008318674B2

(12) United States Patent
Schense et al.

(10) Patent No.: US 8,318,674 B2
(45) Date of Patent: Nov. 27, 2012

(54) LOCAL TREATMENT OF BONE DEFECTS

(75) Inventors: Jason Schense, Zurich (CH); John Watson, Zumikon (CH); Isabelle Arrighi, Zurich (CH)

(73) Assignee: Kuros Biosurgery AG, Zurich (CH)

( * ) Notice: Subject to any disclaimer, the term of this patent is extended or adjusted under 35 U.S.C. 154(b) by 30 days.

(21) Appl. No.: 11/326,924

(22) Filed: Jan. 6, 2006

(65) Prior Publication Data
US 2007/0010440 A1    Jan. 11, 2007

Related U.S. Application Data

(60) Provisional application No. 60/642,848, filed on Jan. 10, 2005, provisional application No. 60/641,830, filed on Jan. 6, 2005.

(51) Int. Cl.
*A61K 38/29* (2006.01)
*A61K 38/00* (2006.01)
*C07K 14/635* (2006.01)
*A61P 19/08* (2006.01)
*A61P 19/10* (2006.01)
*A61P 5/18* (2006.01)
*C12N 15/00* (2006.01)

(52) U.S. Cl. .................. 514/11.8; 514/16.7; 514/16.9; 435/69.7; 424/425

(58) Field of Classification Search .................. None
See application file for complete search history.

(56) References Cited

U.S. PATENT DOCUMENTS

| 4,086,196 | A |   | 4/1978  | Tregear          |         |
|-----------|---|---|---------|------------------|---------|
| 4,613,665 | A |   | 9/1986  | Larm             |         |
| 4,810,784 | A |   | 3/1989  | Larm             |         |
| 4,917,702 | A | * | 4/1990  | Scheicher et al. | 424/423 |
| 5,069,905 | A |   | 12/1991 | Lidor et al.     |         |
| 5,100,668 | A |   | 3/1992  | Edelman et al.   |         |
| 5,171,670 | A |   | 12/1992 | Kronenberg et al.|         |
| 5,202,247 | A |   | 4/1993  | Kilburn et al.   |         |
| 5,428,014 | A |   | 6/1995  | Labroo et al.    |         |
| 5,504,001 | A |   | 4/1996  | Foster           |         |
| 5,510,370 | A | * | 4/1996  | Hock             | 514/443 |
| 5,529,986 | A |   | 6/1996  | Larsson et al.   |         |
| 5,561,982 | A |   | 10/1996 | Tunkel et al.    |         |
| 5,582,862 | A |   | 12/1996 | Reed             |         |
| 5,641,670 | A |   | 6/1997  | Treco et al.     |         |
| 5,693,341 | A |   | 12/1997 | Schroeder et al. |         |
| 5,747,456 | A |   | 5/1998  | Chorev et al.    |         |
| 5,773,577 | A |   | 6/1998  | Capello          |         |
| 5,814,603 | A |   | 9/1998  | Oldenburg et al. |         |
| 5,840,837 | A |   | 11/1998 | Krstenansky et al.|        |
| 5,874,308 | A |   | 2/1999  | Kilburn et al.   |         |
| 5,874,500 | A |   | 2/1999  | Rhee et al.      |         |
| 5,877,153 | A |   | 3/1999  | Harris et al.    |         |
| 5,958,874 | A |   | 9/1999  | Clark et al.     |         |
| 6,054,122 | A |   | 4/2000  | MacPhee et al.   |         |
| 6,117,425 | A |   | 9/2000  | MacPhee et al.   |         |
| 6,136,564 | A |   | 10/2000 | Kopetzki et al.  |         |
| 6,197,325 | B1|   | 3/2001  | MacPhee et al.   |         |
| 6,206,957 | B1|   | 3/2001  | Driessens et al. |         |
| 6,221,854 | B1|   | 4/2001  | Radomsky         |         |
| 6,331,422 | B1|   | 12/2001 | Hubbell          |         |
| 6,372,257 | B1| * | 4/2002  | Marchosky        | 424/488 |
| 6,468,731 | B1|   | 10/2002 | Hubbell          |         |
| 6,559,119 | B1|   | 5/2003  | Burgess et al.   |         |
| 6,960,452 | B2|   | 11/2005 | Hubbell et al.   |         |
| 7,026,292 | B1| * | 4/2006  | Lee et al.       | 514/12  |
| 7,045,105 | B2|   | 5/2006  | Lagow            |         |
| 7,052,856 | B2|   | 5/2006  | Ting             |         |
| 2003/0103957 | A1 |   | 6/2003 | McKerracher   |         |
| 2003/0166833 | A1 | * | 9/2003 | Lutolf et al. | 530/300 |
| 2003/0180376 | A1 | * | 9/2003 | Dalal et al.  | 424/602 |
| 2003/0187232 | A1 |   | 10/2003| Hubbell et al.|         |
| 2004/0002770 | A1 | * | 1/2004 | King et al.   | 623/23.51 |
| 2005/0163817 | A1 |   | 7/2005 | Masters et al.|         |
| 2005/0175665 | A1 | * | 8/2005 | Hunter et al. | 424/423 |
| 2007/0254011 | A1 |   | 11/2007| Schnabelrauch et al.|   |

FOREIGN PATENT DOCUMENTS

| DE | 200 10 297   | 8/2000  |
| EP | 725 145      | 8/1996  |
| EP | 950 665      | 10/1999 |
| WO | WO 89/00051  | 1/1989  |
| WO | WO 90/05177  | 5/1990  |
| WO | WO 92/02620  | 2/1992  |
| WO | WO 92/09301  | 6/1992  |
| WO | WO 92/22312  | 12/1992 |
| WO | WO 94/20133  | 9/1994  |
| WO | WO 95/05396  | 2/1995  |

(Continued)

OTHER PUBLICATIONS

Paciorek et al., 2007 Annual Fall Meeting of the BMES, Sep. 26-29, 2007, see poster Abstract P2.199.*
Saraph et al., J. Pediatr.Orthop., Sep.-Oct. 2004; vol. 24(5):568-73.*
Adams, et al., "Roles of ephrinB ligands and EphB receptors in cardiovascular development: demarcation of arterial/venous domains, vascular morphogenesis, and sprouting angiogenesis," *Genes & Development* 13:295-306 (1999).
Baumgartner, et al., "Constitutive expression of phVEGF165 after intramuscular gene transfer promotes collateral vessel development in patients with critical limb ischemia," *Circulation*, 97:1114-1123 (1998).
Besson, et al., "Synthetic peptide substrates for a conductimetric assay of *Pseudomonas aeruginosa* elastase", *Analytical Biochemistry*, 237(2):216-223 (1996).

(Continued)

*Primary Examiner* — Xiaozhen Xie
(74) *Attorney, Agent, or Firm* — Pabst Patent Group LLP

(57) ABSTRACT

A method of local treatment of specific bone defects such as osteoporosis or bone cysts comprises the step of local administration of a formulation comprising a fusion peptide containing a first domain comprising PTH or BMP 2 or BMP 7, and a second domain comprising a covalently crosslinkable substrate domain; and a material suitable of forming a biodegradable matrix suitable for cellular growth or in-growth, wherein the fusion peptide is covalently linked to the matrix. In one embodiment, the matrix contains one or more contrast agents, and is preferably formed in the absence of a growth factor. The matrix may be used in the treatment of fluid-filled cysts such as Tarlov cysts, ovarian cysts, arachnoid cysts, aneurysmal bone cysts or hepatic cysts.

26 Claims, 1 Drawing Sheet

FOREIGN PATENT DOCUMENTS

| WO | WO 95/23611 | 9/1995 |
|---|---|---|
| WO | WO 96/17633 | 6/1996 |
| WO | WO 99/31137 | 6/1999 |
| WO | WO 00/10596 | 3/2000 |
| WO | WO 00/44808 | 8/2000 |
| WO | WO 02/085422 | 10/2000 |
| WO | WO 00/64481 | 11/2000 |
| WO | WO 03/040235 | 5/2003 |
| WO | WO 03/052091 | 6/2003 |
| WO | WO 2004/071543 | 8/2004 |

OTHER PUBLICATIONS

Blaess, et al., "Structural analysis of the sixth immunoglobulin-I ike domain of mouse neural cell adhesion molecule L1 and its interactions with Ov03, 0IIb03, and 05001 integrins," *J Neurochem*, 71:2615-2625 (1998).

Bonadio, et al., "Localized, direct plasmid gene delivery in vivo: prolonged therapy results in reproducible tissue regeneration" *Nat Med.*, 5(7):753-9 (1999).

Borrajo, et al., "Derivatized Cyclodextrins as peptidometics: Influence on Neurite Growth," *Bioorganic and Medicinal Chemistry Letters*, 7:1185-90 (1997).

Brooks, et al., "Requirement of vascular integrin □v□3 for angiogenesis," *Science*, 264:569-571 (1994).

Bruckner, "EphrinB ligands recruit GRIP family PDZ adaptor proteins into raft membrane microdomains," *Neuron*, 22:511-524 (1999).

Calderwood, et al., "Integrins and actin filaments: reciprocal regulation of cell adhesion and signaling," *J Biol Chem*, 275:22607-22610 (2000).

Camarata, et al., "Sustained Release of Nerve Growth Factor from Biodegradable Polymer Microspheres," *Neurosurgery Online*, 30(3) 313-319 (1992).

Cardin, et al., "Molecular Modeling of Protein-Glycosaminoglycan Interactions," *Arterioscler Thromb Vasc Biol*, 9:21-32 (1989).

Conover, et al., "Disruption of Eph/ephrin signaling affects migration and proliferation in the adult subventricular zone," *Nature Neuroscience*, 3(11):1091-3324 (2000).

Coombs, et al., "Directing sequence-specific proteolysis to new targets. The influence of loop size and target sequence on selective proteolysis by tissue-type plasminogen activator and urokinase-type plasminogen activator", *J. Biol. Chem.*, 273(8):4323-4328 (1998).

Coussons, et al. "Factors that govern the specificity of transglutaminase-catalysed modification of proteins and peptides" *Biochemical L.*, 282:929-30 (1992).

Dalva, et al., "EphB receptors interact with NMDA receptors and regulate excitatory synapse formulation," *Cell*, 103:945-956 (2000).

DeBlois, et al., "Heparin-fibroblast growth factor-fibrin complex: in vitro and in vivo applications to collagen-based materials", *Biomaterials.*, 15(9):665-72 (1994).

Dedhar and Hannigan, "Integrin cytoplasmic interactions and bidirectional transmembrane signaling," *Current Opinion in Cell Biology*, 8:657-669 (1996).

Dimilla, et al., "Mathematical model for the effects of adhesion and mechanics on cell migration speed," *Biophys. J.*, 60(1):15-37 (1991).

Dinbergs, et al., "Cellular response to transforming growth factor-beta1 and basic fibroblast growth factor depends on release kinetics and extracellular matrix interactions," *J. Biol. Chem.*, 271(47):29822-9 (1996).

Downs, et al., "Calcium Alginate Beads as a Slow-Release System for Delivering Angiogenic Molecules in Vivo and In Vitro," *Journal of Cellular Physiology*, 152:422-429 (1992).

Edelman, et al., "Perivascular and intravenous administration of basic fibroblast growth factor: vascular and solid organ deposition," *Proc. Natl. Acad. Sci. U. S. A.*, 90(4):1513-7 (1993).

Edelman, et al., "Basic fibroblast growth factor enhances the coupling of intimal hyperplasia and proliferation of vasa vasorum in injured rat arteries," *J. Clin. Invest.*, 89(2):465-73 (1992).

Edelman, et al., "Controlled and modulated release of basic fibroblast growth factor," *Biomaterials.*, 12(7):619-26 (1991).

Edgar, et al., "The heparin-binding domain of laminin is responsible for its effects on neurite outgrowth and neuronal survival," *EMBO J.*, 3(7):1463-8 (1984).

Eliceiri and Cheresh, "The role of αv integrins during angiogenesis: insights into potential mechanisms of action and clinical development," *Journal of Clinical Investigation*, 103:1227-1230 (1999).

Esposito and Caputo, "Mammalian transglutaminases. Identification of substrates as a key to physiological function and physiopathological relevance", *FEBS J.*, 272(3):615-31 (2005).

Fasol, et al., "Experimental use of a modified fibrin glue to induce site-directed angiogenesis from the aorta to the heart," *Journal of Thoracic and Cardiovascular Surgery*, 107:1432-9 (1994).

Felding-Habermann, et al., "A single immunoglobulin-like domain of the human neural cell adhesion molecule L1 supports adhesion by multiple and platelet integrins," *J Cell Biol*, 139:1567-1581 (1997).

Feng, et al., "Roles for ephrins in positionally selective synaptogenesis between motor neurons and muscle fibers," *Neuron*, 25:295-306 (2000).

Ferrara and Alitalo, "Clinical applications of angiogenic growth factors and their inhibitors," *Nature Medicine*, 5:1359-1364 (1999).

Ferrara, "Molecular and biological properties of vascular endothelial growth factor," *J Mol Med*, 77:527-543 (1999).

Folkman, "Angiogenesis in cancer, vascular, rheumatoid and other disease," *Nature Medicine*, 1:27-31 (1995).

Gale, et al., "Ephrin-B2 selectivity marks arterial vessels and neovascularization sites in the adult, with expression in both endothelial and smooth-muscle cells," *Developmental Biology*, 230:151-160 (2001).

Giannelli, et al., "Transforming growth factor-beta1 triggers hepatocellular carcinoma invasiveness via alpha3beta1 integrin", *Am J Pathol.*, 161(1):183-93 (2002).

Götz, et al., "Neurotrophin-6 is a new member of the nerve growth factor family," *Nature*, 372(6503):266-9 (1994).

Grainger, et al., "Poly(dimethylsiloxane)-poly(ethylene oxide)-heparin block copolymers. I. Synthesis and Characterization," *J. Biomed. Mater Res.*, 22(3): 231-249 (1988).

Griesler, et al., "Enhanced endothelial of expanded polyethrafluoroethylene grafts by fibroblast growth factor type 1 pretreatment," *Surgery*, 112:244-255 (1992).

Groenen, et al., "The carboxy-terminal lysine of alpha B-crystallin is an amine-donor substrate for tissue transglutaminase", *Eur J Biochem.*, 205(2):671-4 (1992).

Grootjans, et al., "Substrate requirements for transglutaminases. Influence of the amino acid residue preceding the amine donor lysine in a native protein", *J Biol Chem.*, 270(39):22855-8 (1995).

Hall, "Molecular properties of fibrin-based matrices for promotion of angiogenesis in vitro," *Microvascular Research*, 62:315-326 (2001).

Hall, et al., "Trimerization of cell adhesion molecule L1 mimics clustered L1 expression on the cell surface: Influence on L1-Ligand interactions and on promotion of neurite outgrowth," *J of Neurochemistry*, 75:336-346 (2000).

Hammoud, et al., "Management of coronary artery disease: Therapeutic options in patients with diabetes," *J Am. Col. Cardiology*, 36:355-65 (2000).

Harada, et al., "Basic fibroblast growth factor improves myocardial function in chronically ischemic porcine hearts," *J. Clin. Invest.*, 94(2):623-30 (1994).

Hata, et al., "Binding of lipoprotein lipase to heparin. Identification of five critical residues in two distinct segments of the amino-terminal domain," *J. Biol. Chem.*, 268(12):8447-57 (1993).

Haugen, et al, "Central and peripheral neurite outgrowth differs in preference for heparin-binding versus integrin-binding sequences," *J. Neurosci.*, 12(6):2034-42 (1992).

Herbert, et al., "Effects of fibinolysis on neurite growth from dorsal root ganglia cultured in two- and three-dimensional fibrin gels," *J. Comp. Neurol.*, 365(3):380-91 (1996).

Herbert, et al., "Effects of fibrin micromorphology on neurite growth from dorsal root ganglia cultured in three-dimensional fibrin gels," *J. Biomed. Mat. Res.*, 40(4):551-9 (1998).

Hern, et al., "Incorporation of adhesion peptides into nonadhesive hydrogels useful for Tissue Resurfacing" *J. Biomed. Mater. Res.*, 39:266-276 (1998).

Houle & Johnson, "Nerve growth factor (NGF)-treated nitrocellulose enhances and directs the regeneration of adult rat dorsal root axons through intraspinal neural tissue transplants," *Neuroscience Letters*, 103:17-23 (1989).

Hubbell, "Bioactive biomaterials" *Curr. Opinion Biotechnol.*, 10(2):123-129 (1999).

Humphries, "Integrin activation: the link between ligand binding and signal transduction," *Curr Opin Cell Biol*, 8:632-640 (1996).

Ilan, et al., "Distinct signal transduction pathways are utilized during the tube formation and survival phases of in vitro angiogenesis," *J of Cell Science*, 111:3621-3631 (1998).

Ingber and Folkman, "How does extracellular matrix control capillary morphogenesis?" *Cell*, 58:803-805 (1989).

Jeong, et al., "The fibronectin•binding domain of transglutaminase", *J Biol Chem.*, 270(10):5654-8 91995).

Kallapur, et al, "The neural cell adhesion molecule (NCAM) heparin binding domain binds to cell surface heparan sulfate proteoglycans," *J. Neuro. Res.*, 33(4):538-48 (1992).

Kaneda, et al., "Midkine, a heparin-binding growth/differentiation factor, exhibits nerve cell adhesion and guidance activity for neurite outgrowth in vitro," *J. Biochem.*, 119(6):1150-6 (1996).

Kang, et al., "Selective stimulation of endothelial cell proliferation with inhibition of smooth muscle cell proliferation by fibroblast growth factor-1 plus heparin delivered from glue suspensions," *Surgery*, 118:280-287 (1995).

Kiguchi, et al., "Altered expression of epidermal growth factor receptor ligands in tumor promoter-treated mouse epidermis and in primary mouse skin tumors induced by an initiation-promotion protocol," *Mol. Carcinog.*, 22(2):73-83 (1998).

Kinosaki, et al., "Identification of heparin-binding stretches of a naturally occurring deleted variant of hepatocyte growth factor (dHGF)," *Biochim. Biophys. Acta.*, 1384(1):93-102(1998).

Kleinman, et al., "The laminins: a family of basement membrane glycoproteins important in cell differentiation and tumor metastases," *Vitam. Horm.*, 47:161-86 (1993).

Lee, et al., "Analysis of affinity and structural selectivity in the binding of proteins to glycosaminoglycans: Development of a sensitive electrophoretic approach," *Biochemistry*, 88:2768-2772 (1991).

Lin, et al., "Purification and Initial Characterization of Rat B49 Glial Cell Line-Derived Neurotrophic Factor," *Journal of Neurochemistry*, 63(2):758-768 (1994).

Lopez, et al., "Basic fibroblast growth factor in a porcine model of chronic myocardial ischemia: a comparison of angiographic, echocardiographic and coronary flow parameters,"*J. Pharmacol. Exp. Ther.*, 282(1):385-90 (1997).

Lopez, et al., "Local perivascular administration of basic fibroblast growth factor: drug delivery and toxicological evaluation," *Drug Meta. Dispos.*, 24(8):922-4 (1996).

Lorsordo, et al., "Gene therapy for myocardial angiogenesis. Initial clinical results with direct myocardial injection of phVEGF165 as sole therapy for myocardial ischemia," *Circulation*, 98:2800-2804 (1998).

Ludbrook, et al., "The integrin alphavbeta3 is a receptor for the latency-associated peptides of transforming growth factors beta1 and beta3", *Biochem J.*, 369(Pt 2):311-8 (2003).

Luginbuehl, et al., "Localized delivery of growth factors for bone repair" *European Journal of Pharmaceutics and Biopharmaceutics*, 58:197-208 (2004).

Lyon, et al., "The Interaction of the Transforming Growth Factor-βs with Heparin/Heparan Sulfate is Isoform-specific," *The Journal of Biological Chemistry*, 272(29):18000-18006 (1997).

Martin and Timpl, "Laminin and other basement membrane components," *Annu. Rev. Cell.Dev. Biol.*, 3:57-85 (1987).

Massia, et al., "An RGD spacing of 440 nm is sufficient for integrin alpha V beta 3-mediated fibroblast spreading and 140 nm for focal contact and stress fiber formation," *J. Cell. Biol.*, 114(5):1089-100(1991).

Maysinger, et al., "Microencapsulated nerve growth factor: effects on the forebrain neurons following devascularizing cortical lesions," *Neuroscience Letters*, 140:71-74 (1992).

McCaffrey, et al., "Transforming growth factor-beta 1 is a heparin-binding protein: identification of putative heparin-binding regions and isolation of heparins with varying affinity for TGF-beta 1," *J. Cell. Physiol.*, 152(2):430-40 (1992).

Montgomery, et al., "Human neural cell adhesion molecule L1 and Rat homologue NILE are ligands for integrin αγβ3," *J Cell Biol*, 132:475-485 (1996).

Monsonego, et al., "Factor XIIIa as a nerve-associated transglutaminase", *FASEB J.*, 12(12):1163-71 (1998).

Nehls and Herrmann, "The configuration of fibrin clots determine capillary morphogenesis and endothelial cell migration," *Microvascular Research*, 51:347-364 (1996).

Nesti, et al., "TGF-beta1 calcium signaling increases alpha5 integrin expression in osteoblasts", *J Orthop Res.*, 20(5):1042-9 (2002).

Netzel-Arnett, et al., "Sequence specificities of human fibroblast and neutrophil collagenases", *J. Biol. Chem.*, 266:6747-6755 (1991).

Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites," *Eur. J. Neurosci.*, 8(8):1658-65 (1996).

Pepper, et al., "Angiogenesis: a paradigm for balanced extracellular proteolysis cell migration and morphogenesis," *Enzyme Protein*, 49:138-162 (1996).

Potts, "Parathyroid hormone: past and present", *J Endocrinol.*, 187(3):311-25 (2005).

Powell, et al., "Controlled Release of nerve growth factor from a polymeric implant," *Brain Research* 515:309-311 (1990).

Presta, et al., "Structure-function relationship of basic fibroblast growth factor: site-directed mutagenesis of a putative heparin-binding and receptor-binding region," *Biochem. Biophys. Res. Commun.*, 185(3):1098-107 (1992).

Reddi, "Role of Morphogenetic Proteins in Skeletal Tissue Engineering and Regeneration," *Nature Biotechnol.*, 16:247-252 (1998).

Rixon, et al., "Do the non-catalytic polysaccharide-binding domains and linker regions enhance the biobleaching properties of modular xylanases?" *Appl. Microbiol. Biotechnol.*, 46(5-6): 514-520 (1996).

Rixon, et al., "Parathyroid hormone fragments may stimulate bone growth in ovariectomized rats by activating adenylyl cyclase", *J Bone Miner. Res.*, 9(8):1179-89 (1994).

Rogers, et al., "Neuron-specific interactions with two neurite-promoting fragments of fibronectin," *J. Neurosci.*, 5(2):369-78 (1985).

Rosengart, et al., "Angiogenesis Gene Therapy. Phase I assessment of direct intramyocardial administration of an adenovirus expressing phVEGF165 cDNA to individuals with clinically significant severe coronary artery disease," *Circulation*, 100:468-474 (1999).

Rout, et al., "Transforming growth factor-beta1 modulates expression of adhesion and cytoskeletal proteins in human peritoneal fibroblasts", *Fertil Steril.*, 78(1):154-61 (2002).

Ruoslahti & Engvall, "Perspectives series: Cell adhesion in vascular biology," *J Clin Invest*, 99:1149-1152 (1997).

Sakata & Aoki, et al., "Cross-linking of α2-plasmin inhibitor to fibrin by fibrin-stabilizing factor," *J Clin Invest*, 65:290-297 (1980).

Sakiyama, et al., "Incorporation of heparin-binding peptides into fibrin gels enhances neurite extension: an example of designer matrices in tissue engineering," *FASEB J* 13(15): 2214-24 (1999).

Sakiyama-Elbert and Hubbell, "Controlled release of nerve growth factor from a heparin-containing fibrin-based cell ingrowth matrix" *Journal of Controlled Release*, 69:149-158 (2000).

Sakiyama-Elbert, et al., "Development of fibrin derivatives for controlled release of heparin binding growth factors," *J. Controlled Release*, 65(3) 389-402 (2000).

Sakiyama-Elbert, et al., "Development of growth factor fusion proteins for cell-triggered drug delivery" *FASEB J.*, 15:1300-1302 (2001).

Schense, et al., "Enzymatic incorporation of bioactive peptides into fibrin matrices enhances neurite extension" *Nature Biotechnology*, 18:415-419 (2000).

Schense, et al., "Cross-linking exogenous bifunctional peptiedes into fibrin gels with factor XIIIa," *Bioconjug. Chem.*, 10(1): 75-81 (1999).

Schroeder-Tefft et al., "Collagen and heparin matrices for growth factor delivery," *Journal of Controlled Release*, 49:291-298 (1997).

Schumacher, et al., "Induction of neoangiogenesis in ischemic myocardium by human growth factors," *Circulation*, 97:645-650 (1998).

Seibel, et al., Transfection of mitochnondria: strategy towards a gene therapy of mitochondrial DNA diseases, *Nucleic Acids Res.*, 23(1): 10-7 (1995).

Sellke, et al., "Basic FGF enhances endothelium-dependent relaxation of the collateral-perfused coronary microcirculation," *Am. J. Physiol.* 267(4 Pt 2):H1303-11 (1994).

Shin, et al., "Expression of EphrinB2 identifies a stable genetic difference between arterial and venous vascular smooth muscle as well as endothelial cells, and of adult neovascularization," *Developmental Biology*, 230:139-150 (2001).

Shireman, et al., "Modulation of vascular cell growth by local cytokine delivery from fibrin glue suspensions," *J Vasc Surg*, 19:852-62 (1999).

Smith, et al., "Rapid Identification of Highly Active and Selective Substrates for Stromelysin and Matrilysin Using Bacteriophage Peptide Display Libraries", *J. Biol. Chem.*, 270:6440-6449 (1995).

Spillman, et al., "Defining the interleukin-8-binding domain of heparan sulfate," *J. Biol. Chem.*, 273(25):15487-93 (1998).

Steffen, et al., "Characterization of cell-associated and soluble forms of connective tissue growth factor (CTGF) produced by fibroblast cells in vitro," *Growth Factors*, 15(3):199-213 (1998).

Stein, et al., "Eph receptors discriminate specific ligand oligomers to determine alternative signaling complexes, attachment, and assembly responses," *Genes & Development*, 12:667-678 (1998).

Studier, et al., "Use of T7 RNA polymerase to direct expression of cloned genes," *Methods Enzymol*, 185:60-89 (1990).

Takagi and Doolittle, "Amino acid sequence studies on the alpha chain of human fibrinogen. Location of four plasmin attack points and a covalent cross-linking site", *Biochem.*, 14:5149-5156 (1975).

Takeshita, et al., "Therapeutic Angiogenesis. A single intraarterial bolus of vascular endothelial growth factor augments revascularization in a rabbit ischemic hind limb model," *J Clin Invest*, 93:662-670 (1994).

Tashiro, et al., "A synthetic peptide containing the IKVAV sequence from the A chain of laminin mediates cell attachment, migration, and faults outgrowth," *J. Biol. Chem.*, 264(27):16174-82 (1989).

Tessler, et al., "Heparin modulates the interaction of VEGF165 with soluble and cell associated flk-1 receptors," *J. Biol. Chem.*, 269(17):12456-61 (1994).

Thompson, et al., "Site-directed neovessel formation in vivo," *Science*, 241:1349-1352 (1988).

Tyler-Cross, et al., "Heparin binding domain peptides of antithrombin III: analysis by isothermal titration calorimetry and circular dichroism spectroscopy," *Protein Sci.*, 3(4):620-7 (1994).

Usui, et al., "Propolypeptide of von Willebrand factor serves as a substrate for factor XIIIa and is cross-linked to laminin", *J Biol Chem.*, 268(17):12311-6 (1993).

Wang, et al., "Molecular distinction and angiogenesis interaction between embryonic arteries and veins revealed by ephrin-B2 and its receptor Eph-B4," *Cell*, 93:741-753 (1998).

Weatherford, et al., "Vascular endothelial growth factor and heparin in a biologic glue promotes human aortic endothelial cell proliferation with aortic smooth muscle cell inhibition," *Surgery*, 433-439 (1996).

Yamada, "Adhesive recognition sequences," *J. Biol. Chem.*, 266(20):12809-12 (1991).

Yamada, et al., "Characterization of fibronectin interactions with glycosaminoglycans and identification of active proteolytic fragments", *J Biol Chem.*, 255(13):6055-63 (1980).

Yanish-Perron, et al., "Improved M13 phage cloning vectors and host strains: nucleotide sequences of the M13mp18 and pUC19 vectors," *Gene*, 33(1):103-19 (1985).

Zisch, et al., "Covalently conjugated VEGF-fibrin matrices for endothelialization" *Journal of Controlled Release*, 72:101-113 (2001).

Zucker and Katz, "Platelet factor 4: production, structure, and physiologic and immunologic action," *Proc. Soc. Exp. Biol. Med.*, 198(2):693-702 (1991).

Carr et al., "Effects of ionic and nonionic contrast media on clot structure, platelet function and thrombolysis mediated by tissue plasminogen activator in plasma clots", *Haemostasis*, 25(4):172-B1 (1995).

Maeno, et al., "The effect of calcium ion concentration on osteoblast viability, proliferation and differentiation in monolayer and 3D culture," *Biomaterials*, 26: 4847-55 (2005).

Poole and Reeve, "Parathyroid hormone—a bone anabolic and catabolic agent," *Current Opinion in Pharmacology*, 5: 612-7 (2005).

Schilling, et al., "Osteoclasts and biomaterials," *European Journal of Trauma*, 2: 107-13 (2006).

* cited by examiner

LOCAL TREATMENT OF BONE DEFECTS

CROSS-REFERENCE TO RELATED APPLICATIONS

This application claims priority to U.S. Ser. No. 60/641,830, filed Jan. 6, 2005 and U.S. Ser. No. 60/642,848, filed Jan. 10, 2005.

FIELD OF THE INVENTION

The present invention relates to a method of local treatment of bone cysts and a prophylactic local treatment of areas in non-healthy bones affected by osteoporosis.

BACKGROUND OF THE INVENTION

Osteoporosis

Bone loss is a natural part of aging with both men and women losing bone mass at a rate of 0.6 to 1.2% per year starting on average between the ages of 40 to 50. Following the menopause in women bone loss accelerates to 2-3% per year. However, in particular in post-menopausal women, the rate of bone loss may increase dramatically. This disease state is called osteoporosis. Osteoporosis is of major world-wide significance, affecting nearly 200 million people. At present 10 million people in the US suffering from osteoporosis and a further 18 million have osteopenia putting them at risk of developing the disease. Of this at-risk population, 80% are women. Osteoporosis is a systemic skeletal disease generally affecting the entire skeleton in which the overall mass of bone is decreased and the structure of the bone deteriorates, which increases bone porosity. These changes in bone mass and structure reduce the overall strength of the bone and make it prone to fracture.

Osteoporosis is a complex interaction between systemic hormones and local factors and the exact cellular mechanisms of osteoporosis remain to be defined. As a result the current therapies do not tackle directly the causes of the condition. For example, derivatives of the most commonly used therapeutics, bisphosphonates, are at best only 50% efficacious in reducing the incidence of fracture. Bisphosphonates currently approved for use include, alendronate (FOSAMAX®), etidronate (DIDROCAL®) and risedronate (ACTONEL®). Given either in tablet form or intravenously, bisphosphonates are a family of drugs used to prevent and treat osteoporosis by coating bones and preventing osteoclast activity.

Bone Cysts

Bone cysts are benign unilocular lytic areas usually in the proximal end of a long bone with well defined and narrow endosteal margins. An unicameral bone cyst, otherwise known as a simple bone cyst, is a fluid-filled cavity in the bone, lined by compressed fibrous tissue. It usually occurs in the long bones of a growing child, especially the upper part of the humerus (50-60% of the time) or the upper part of the femur (25-30% of the time). Other bones, however, can be affected. These cysts usually affect children primarily between the ages of 5 to 15, but can affect older children or adults. In older children and adults, they tend to occur in flat bones (such as the pelvis, jaw, skull or rib cage) or in the large heel bone (calcaneus).

Unicameral bone cysts are considered benign. They do not metastasize (spread) beyond the bone. Some heal spontaneously, while others enlarge. More invasive cysts can grow to fill most of the bone's metaphysis (the transitional zone where the shaft of the bone joins the end of the bone) and cause what is known as a pathological fracture. A more invasive cyst could also destroy the bone's growth plate, leading to shortening of the bone. These cysts are sometimes classified as either "active" or "latent." An active cyst is adjacent to the growth plate and tends to enlarge, causing the problems mentioned above. A latent cyst is one that is more apt to heal with treatment because the growth plate has migrated away from the cyst.

Current treatment is aimed primarily at preventing recurrent fractures. The following surgical procedures are applied currently: Curettage/Bone Grafting (a surgical scraping of the cyst with a special instrument called a curette that has a scoop, loop or ring at its tip), steroid injection, or bone marrow injection.

Periarticular subchondral bone cysts, also referred to as subchondral cystic lesions (SCLs), may occur in young horses and are a similar clinical entity to unicameral bone cysts in humans. They are commonly recognised pathological entities which often lead to lameness in young horses. The most common site at which SCLs are encountered is in the stifle (the equivalent of the human knee). Specifically, bone cysts are found in the main weight bearing aspect of the stifle (the medial femoral condyle) and rarely at other locations within the joint (proximal lateral tibia and lateral femoral condyle). SCLs are radiolucent areas of bone that, depending on their stage of development, are well demarcated from the surrounding tissue through a sclerotic rim and are generally filled with fibrous connective tissue and serous fluid resembling synovial fluid. In horses a joint connection to the overlying articular cartilage surface can be found in a third of cases. The size of a medial femoral cyst varies from shallow dome-shaped defects (approximately 8 mm×3 mm) to large ovoid-shaped cysts of 40 mm×30 mm.

Treatment options for SCLs causing lameness include long term rest, anti-arthritic and intra-articular corticosteroid therapy and surgery. Conservative therapy, which may require nine to twelve months of paddock rest, has been associated with resolution of lameness. Unfortunately the number of horses managed by conservative therapy that have been evaluated in the veterinary literature is very limited, but success rates are approximately 50%.

Numerous surgical techniques have been used in the treatment of equine bone cysts. Current recommended treatment involves arthroscopic removal (curettage) of the cystic contents, cyst lining and the overlying unsupported cartilage. Additional techniques used in an attempt to enhance healing and improve outcome have included bone drilling and grafting, both of which are now considered to offer no benefit. Further, bone cysts may continue to expand and finally lead to secondary osteoarthritis in the equine joint.

Over the past twenty years, several bioactive factors have been investigated for their ability to influence the regeneration of bone tissue. Parathyroid hormone (PTH) is an 84 amino acid peptide that is made and secreted by the parathyroid gland. This hormone plays a primary role in controlling serum calcium levels through its action on various tissues, including bone. Studies in human with various forms of parathyroid hormone have demonstrated an anabolic effect on bone when applied systemically. This makes parathyroid hormone interesting for the systemic treatment of osteoporosis and related bone disorders (U.S. Pat. No. 5,747,456 to Chorev, et al. and WO 00/10596 to Eli Lilly & Co.). The parathyroid hormone acts on cells by binding to a cell surface receptor. This receptor is known to be found on osteoblasts, the cells that are responsible for forming new bone.

The N-terminal 34 amino acid domain of the human parathyroid hormone has been reported to be biologically equivalent to the full length parathyroid hormone. Parathyroid hormone $_{1-34}$ and its mode of action were first reported in U.S. Pat. No. 4,086,196. Research has been done on parathyroid hormone $_{1-34}$ and other truncated versions of the native human parathyroid hormone form, as e.g. 1 to 25, 1 to 31 and 1 to 38 (see e.g. Rixon R H, et al., *J Bone Miner. Res.,* 9 (8): 1179-89 (August 1994).

The mechanism by which PTH influences bone remodelling is complicated, which has led to conflicting results and subsequently, a significant number of studies on the exact mechanisms involved. It has been demonstrated that if PTH is administered systemically in a continuous manner, that the bone density will decrease. In contrast, it has been reported that if the same molecule is administered systemically in pulsatile fashion, the bone density will increase (see e.g. WO 99/31137 to Eli Lilly & Co.). This apparent contradiction can be explained by the mechanism in which PTH modulates bone remodelling and subsequently the observable parameter of bone density. Within mature bone, the PTH receptor has only been shown to be present on the surface of cells of the osteoblast lineage, but not on osteoclasts. The role that PTH plays in bone remodelling is directed through the osteoblasts as opposed to the osteoclasts. However, the cells at different stages of the osteoblast lineage respond differently when they bind to parathyroid hormone. Therefore, the dramatic differences that are observed when PTH is administered using different methods can be accounted for by understanding the different effects that the same molecule has on the different cells within the osteoblast lineage.

When PTH binds to a mesenchymal stem cell, the cell is induced to differentiate into a preosteoblast. Thus, by adding PTH to the system, there is an increase in the preosteoblast population. However, these preosteoblast cells have the PTH receptor as well, and the subsequent binding of PTH to the receptor on these cells leads to a different response. When PTH binds to the preosteoblast, it results in two separate consequences that lead to bone resorption. First, it inhibits the further differentiation of the preosteoblasts into osteoblasts. Second, it increases the secretion of Interleukin 6 (IL-6) from the preosteoblasts. IL-6 both inhibits preosteoblast differentiation as well as increases preosteoclast differentiation into osteoclasts. This dual response from the cells within the osteoblast lineage is what provides the complex reaction between bone remodelling and PTH exposure. If PTH is dosed periodically for short periods of time, then the mesenchymal stem cells are induced to differentiate into osteoblasts. The short dosing periods then prevent the newly formed preosteoblasts from producing IL-6, preventing activation of the osteoclasts. Therefore, during the intervals of dosing, these newly formed preosteoblasts can further differentiate into osteoblasts, resulting in bone formation. However, if a constant dose of PTH is applied, then the preosteoblasts will have the opportunity to begin producing IL-6, thus activating the osteoclasts and inhibiting themselves, leading to the opposite effect: bone resorption.

Another bioactive factor which has been explored is the group of the bone morphogenetic proteins (BMPs) and transforming growth factors (TGF βs). There are at least 20 structurally and functionally related BMPs and several TGF βs, which are members of the TGF-beta superfamily. BMPs were originally identified as protein regulators of cartilage and bone formation. They are also involved in embryogenesis and morphogenesis of various tissues and organs. BMPs regulate the growth, differentiation, chemotaxis and apoptosis of various cell types, including mesenchymal cells, epithelial cells, hematopoietic cells and neuronal cells. Similar to other TGF-beta family proteins, BMPs are highly conserved across animal species.

Bone morphogenetic proteins 2 and 7 (BMP 2 and 7) are of specific interest in bone or cartilage formation applications. BMP 2 induces the formation of both cartilage and bone. The protein is synthesized as a prepropeptide. Full length human prepropetide BMP 2 is a glycosylated polypeptide having a sequence of 396 amino acids, consisting of a 19 amino acid signal sequence, a 263 amino acid pro region and a 114 amino acid mature segment. Cleavage of the pro-region occurs prior to segregation. The mature form has 7 cysteine moieties and one N-linked glycosylation site. The functional form of the protein consists of two disulfide-linked mature chains. It has been found that BMP 2 variants consisting only of a part of the mature amino acid sequence of BMP 2, such as the amino acids 283 to 396, also exhibit biological activity.

Human BMP 7, or osteogenic protein-1 (Op-1), is a 49 kDa, 431 amino acid preproprotein that is cleaved, similarly to BMP 2, into a 292 amino acid preproregion and a 139 amino acid mature segment. The mature segment contains three potential N-linked glycosylation sites plus seven cysteine residues.

For tissue repair or regeneration, cells must migrate into a wound bed, proliferate, express matrix components or form extracellular matrix, and form a final tissue shape. Multiple cell populations often participate in this morphogenetic response, frequently including vascular and nerve cells. Matrices which have the bioactive factors incorporated therein have been demonstrated to greatly enhance, and in some cases have been found to be essential, for this to occur. Approaches have been made in developing matrices from natural or synthetic origins or a mixture of both. Natural cell in-growth matrices are subject to remodelling by cellular influences, all based on proteolysis, e.g. by plasmin (degrading fibrin) and matrix metalloproteinases (degrading collagen, elastin, etc.). Such degradation is highly localized and occurs only upon direct contact with the migrating cell. In addition, the delivery of specific cell signalling proteins such as growth factors is tightly regulated. In the natural model, macroporous cell in-growth matrices are not used, rather microporous matrices that the cells can degrade, locally and upon demand, as the cells migrate into the matrix, are formed. Due to concerns regarding immunogenicity, expensive production, limited availability, batch variability and purification, matrices based on synthetic precursor molecules, such as modified polyethylene glycol, have been developed for tissue regeneration in and/or on the body.

While much work has been done studying the systemic effects of PTH, as described above, research has hardly explored local or topical administration of PTH. In WO 03/052091, a way of locally administering PTH has been described. WO 03/052091 describes parathyroid hormone as being covalently attached to synthetic and natural matrices, in particular fibrin and polyethyleneglycol-matrices. In that way, parathyroid hormone may be administered locally and released at the site of need in a controlled fashion. It has been shown in WO 03/052091 that this system triggers the formation of bone tissue in healthy bone.

It is the object of the present invention to provide a method of local treatment of areas in non-healthy bones, i.e. bones affected by osteoporosis or, i.e. bones affected by bone cysts and bone tumours.

SUMMARY OF THE INVENTION

It has been surprisingly found that areas of non-healthy bones, e.g. bones or specific bone areas which are affected and weakened by osteoporosis or bone cysts or bone tumours, can be effectively treated by the local administration of bioactive factors. Matrices containing a bioactive factor (also referred to herein as "supplemented matrices") that are suitable for the local regeneration of areas of non-healthy bone or the local increase of bone density in areas of non-healthy bone and methods for making and using the matrices are described herein. In a preferred embodiment the bioactive factor is releasably incorporated into the matrix. The matrix can be formed in-situ at the site of non healthy bone areas or, dependent on the indication, can be formed outside the body and applied to the body in pre-shaped formed through surgery. The bioactive factor is released from the matrix and triggers regeneration of bone tissue locally. Suitable bioactive factors include molecules, peptides and proteins having the capabilities of triggering regeneration of bone tissue. The bioactive factor is preferably PTH or a BMP. The parathyroid hormone can be $PTH_{1-84}$ (native), $PTH_{1-38}$, $PTH_{1-34}$, $PTH_{1-31}$, $PTH_{1-28}$ or $PTH_{1-25}$, or any modified or allelic versions of PTH having the capabilities of triggering regeneration of bone tissue, or $BMP_2$ or $BMP_7$ The most preferred bioactive factors are $PTH_{1-34}$ or $BMP_2$. In one embodiment, the bioactive factor is in a fusion peptide. The fusion peptide contains a first domain comprising the bioactive factor, preferably PTH or BMP, and a second domain comprising a crosslinkable substrate domain.

In a further preferred embodiment, the bioactive factor forms part of a precursor composition suitable for forming a supplemented matrix at the site of need in the affected bone. The composition for forming the supplemented matrix is preferably injectable and formed from liquid (at 25° C.) precursor component(s). One method of administering the supplemented matrix to and/or into areas of non-healthy bone requires at least one liquid precursor component capable of forming a matrix at physiological temperatures and a bioactive factor and applying the precursor component and bioactive factor to and/or into the area of non-healthy bone. The bone defects, i.e. the areas of non-healthy bones are generally bone areas being affected by osteoporosis, bone cysts or bone tumours. In case of osteoporotic bone, the treatment results in a local increase of bone density in the osteoporotic part of the bone, which can be, for example, the femoral neck or vertebra (and thus lower fracture rate of the bone or part of the bone). In that sense the method of treating non-healthy areas of bones with the supplemented matrix as described in the present application is a prophylactic treatment in particular for the prevention of bone fractures. In cases in which the supplemented matrix is applied into or formed in a cleaned cavity of a bone cyst or after removal of a bone tumour, the supplemented matrix induces bone formation in the cavity which serves at restoring the integrity of the bone both functionally, as well as structurally.

Preferably the matrix is a fibrin matrix or a matrix based on polyethyleneglycol.

Cells can also be added to the matrix prior to or at the time of implantation, or even subsequent to implantation, either at or subsequent to crosslinking of the polymer to form the matrix. This may be in addition to or in place of crosslinking the matrix to produce interstitial spacing designed to promote cell proliferation or in-growth.

In one embodiment, the matrix contains one or more contrast agents, and can also be formed in the absence of a growth factor. Generally the contrast agents enable imaging of the distribution and positioning of the formulation during injection and gelation. If the formulation is used without a bioactive factor, the matrix may preferably be used in the treatment of fluid-filled cysts such as Tarlov cysts, ovarian cysts, arachnoid cysts, aneurysmal bone cysts, or hepatic cysts.

DETAILED DESCRIPTION OF THE INVENTION

Figure 1:
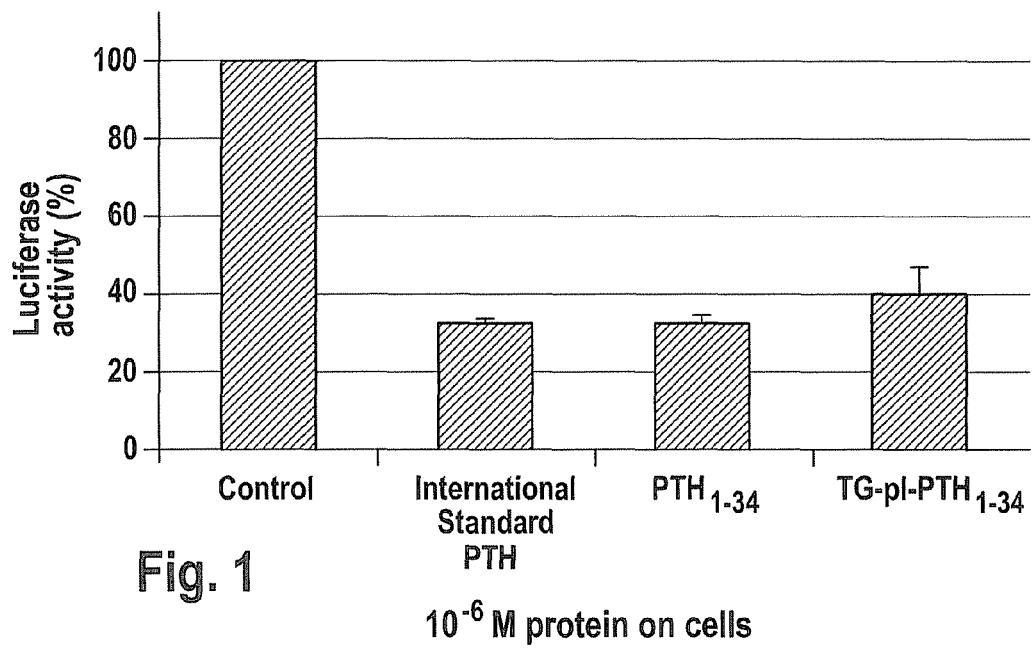
FIG. 1 shows the bioactivity of PTH variants. Cells transfected with a reporter gene linked to a promoter for a PTH receptor were treated with equal amounts of either $PTH_{1-34}$, $TG-pl-PTH_{1-34}$ (described hereinafter) or the international 84 amino acid standard. The inhibition of expression of the luciferase reporter gene was measured and compared to transfected cells that were not exposed to PTH in solution (control).

A method for local treatment of bone defects and structures in non-healthy bones (summarized areas of non-healthy bone) are described herein. Preferably treated are areas in osteoporotic bone and/or bone cysts and/or bone tumours. The method uses natural and synthetic matrices having bioactive factors, in particularly PTH or BMP, releasably incorporated in the matrix. The supplemented matrices are injectable, biocompatible and biodegradable and can be formed in vitro or in vivo, at the time of implantation. The bioactive factor can be incorporated into the matrices and retain its full bioactivity. Particularly preferred bioactive factors $PTH_{1-34}$, BMP 2 or BMP 7 can be releasably incorporated by covalent or non-covalent interaction with the matrix, using techniques that provide control over how and when and to what degree the PTH or BMPs is released, so that the supplemented matrix can be used for tissue repair directly or indirectly, using the supplemented matrix as a controlled release vehicle.

Definitions

"Adhesion site or cell attachment site" as generally used herein refers to a peptide sequence to which a molecule, for example, an adhesion-promoting receptor on the surface of a cell, binds. Examples of adhesion sites include, but are not limited to, the RGD sequence from fibronectin, and the YIGSR (SEQ ID NO: 1) sequence from laminin. Adhesion sites can be optionally incorporated into the matrix by including a substrate domain crosslinkable to the fibrin matrix.

"Biological activity" as generally used herein refers to functional events mediated by a protein of interest. In some embodiments, this includes events assayed by measuring the interactions of a polypeptide with another polypeptide. It also includes assaying the effect which the protein of interest has on cell growth, differentiation, death, migration, adhesion, interactions with other proteins, enzymatic activity, protein phosphorylation or dephosphorylation, transcription, or translation.

"Conjugated unsaturated bond" as generally used herein refers to the alternation of carbon-carbon, carbon-heteroatom or heteroatom-heteroatom multiple bonds with single bonds, or the linking of a functional group to a macromolecule, such as a synthetic polymer or a protein. Such bonds can undergo addition reactions.

"Conjugated unsaturated group" as generally used herein refers to a molecule or a region of a molecule, which contains an alternation of carbon-carbon, carbon-heteroatom or heteroatom-heteroatom multiple bonds with single bonds, which has a multiple bond which can undergo addition reactions. Examples of conjugated unsaturated groups include, but are not limited to vinyl sulfones, acrylates, acrylamides, quinones, and vinylpyridiniums, for example, 2- or 4-vinylpyridinium and itaconates.

"Contrast agents" as generally used herein means a molecule or substance used to increase a contrast of an image and which enables monitoring of the substance or molecule in the body.

"Cross-linking" as generally used herein means the formation of covalent linkages.

"Crosslink density" as generally used herein refers to the average molecular weight between two crosslinks ($M_c$) of the respective molecules.

"Equilibrium state" as generally used herein as the state in which a hydrogel undergoes no mass increase or loss when stored under constant conditions in water.

"Equivalent weight" as generally used herein refers to mmol of functional group/g of substance.

"Fibrin Matrix" as generally used herein means the product of a process in which substantially all of the precursor components fibrinogen and thrombin crosslink in the presence of a calcium source and Factor XIIIa to form a three-dimensional network. The terms matrix, gel and three-dimensional or polymeric network are used synonymously.

"Functionalize" as generally used herein refers to modifying a molecule in a manner that results in the attachment of a functional group or moiety. For example, a molecule may be functionalized by the introduction of a molecule which makes the molecule a strong nucleophile or a conjugated unsaturated molecule. Preferably a molecule, for example PEG, is functionalized to become a thiol, amine, acrylate, or quinone. Proteins, in particular, may also be effectively functionalized by partial or complete reduction of disulfide bonds to create free thiols.

"Functionality" as generally used herein refers to the number of reactive sites on a molecule.

"Functionality of the branching points" as generally used herein refers to the number of arms extending from one point in the molecule.

"Fusion peptides or proteins" as generally used herein refers to a peptide or protein which contains at least a first and a second domain. One domain contains a bioactive factor, preferably PTH 1-34, BMP 2 or BMP 7 and the other domain contains a substrate domain crosslinkable to a matrix during or after its formation. An enzymatic or hydrolytic degradation site can also be present between the first and the second domain.

"Matrix" as generally used herein refers to a material intended to interface with biological systems to treat, augment, or replace any tissue or function of the tissue depending on the material either permanently or temporarily. The matrix can serve as a delivery device for bioactive factors incorporated therein and/or as a cell-ingrowth matrix. The matrices described herein are formed from liquid precursor components which are able to form a scaffold in the body at the site of need. The terms "matrix" and "gel" are used synonymously herein. The terms "matrix" and "gel" refer to the composition formed after the precursor components are mixed together. Thus the terms "matrix" and "gel" encompass partially or fully crosslinked polymeric networks. They may be in the form of a liquid, semi-solid, such as a paste, or a solid. Depending on the type of precursor materials, the matrix may be swollen with water but not dissolved in water, i.e. form a hydrogel which stays in the body for a certain period of time.

"Multifunctional" as generally used herein refers to more than one electrophilic and/or nucleophilic functional group per molecule (i.e. monomer, oligo and polymer).

"Naturally occurring precursor components or polymers" as generally used herein refers to molecules which could be found in nature.

"Non-healthy bone or areas of non-healthy bones" as generally used herein refers to bone or parts of the bone, which have disorders caused by structural or genetic deterioration as caused by osteoporosis, local inflammation as in bone cysts or tumour growth as in cancer. Bone fractures in osteoporotic bone are contemplated to be a bone defect in the sense of the present invention.

"Osteoporosis" as generally used herein refers to a systemic, skeletal disease characterized by low bone mass and the structural deterioration of bone tissue, which increases bone porosity and susceptibility to fractures. Bone loss is asymptomatic, some people may not be aware that they have osteoporosis until they suffer bone fractures. Two major types of osteoporosis are known: primary osteoporosis and secondary osteoporosis. Primary osteoporosis is subdivided into Type I osteoporosis, which affects women in whom the onset of menopause has caused accelerated bone loss; and type II osteoporosis, which affects people in whom the aging process has led to a reduction in bone density. Secondary osteoporosis occurs in people who experience bone loss secondary to other diseases or who use certain types of drugs. The wrist, vertebra and hip are at mainly susceptible to osteoporosis related fractures. Preferred is the treatment of osteoporosis type I.

"Non-healthy bone" or "non healthy areas of bone" as generally used herein means bone structure in a diseased state, irrespective of the kind of disease.

"Polyethyleneglycol Matrices" as generally used herein means the product of a process in which at least two precursor polyethyleneglycol components with functional groups crosslink self-selectively with each other to form a three-dimensional crosslinked network. These systems are known and described, such as in WO 03/052091.

"PTH" as used herein includes the human sequence of $PTH_{1-84}$ and all truncated, modified and allelic versions of PTH which exhibit bone formation properties, in particular when incorporated preferably covalently bound to a fibrin matrix. Preferred truncated versions of PTH are $PTH_{1-38}$, $PTH_{1-34}$, $PTH_{1-31}$ or $PTH_{1-25}$. Most preferred is $PTH_{1-34}$. Preferably, the PTH is human PTH, although PTH from other sources, such as bovine PTH, may be suitable.

"Periosteum" as used herein means the outer layer of bones forming a dense, fibrous layer, with the exception of those portions that form a joint structure which covers the entire bone structure and contains the vasculature that nourishes the exterior bone tissue.

"Physiological" as generally used herein means conditions as they can be found in living vertebrates. In particular, physiological conditions refer to the conditions in the human body such as temperature and pH. Physiological temperatures mean in particular a temperature range of between 35° C. to 42° C., preferably around 37° C.

"Polymeric network" as generally used herein means the product of a process in which substantially all of the monomers, oligos or polymers are bound by intermolecular covalent linkages through their available functional groups to result in one huge molecule.

"Strong nucleophile" as generally used herein refers to a molecule which is capable of donating an electron pair to an electrophile in a polar-bond forming reaction. Preferably the strong nucleophile is more nucleophilic than water at physiologic pH. Examples of strong nucleophiles are thiols and amines.

"Synthetic precursor molecules" as generally used herein refers to molecules which do not exist in nature.

"Self selective reaction" as generally used herein means that the first precursor component of a composition reacts much faster with the second precursor component of the composition and vice versa than with other compounds present in a mixture or at the site of the reaction. As used herein, the nucleophile preferentially binds to an electrophile and an electrophile preferentially binds to a strong nucleophile, rather than to other biological compounds.

"Swelling" as generally used herein refers to the increase in volume and mass by uptake of water by the matrix. The terms "water-uptake" and "swelling" are used synonymously throughout this application.

"Supplemented matrix" as generally used herein refers to a matrix in which bioactive factors, optionally fusion peptides, are releasably incorporated therein. The bioactive factors are incorporated through either covalent or non-covalent interaction.

I. Supplemented Matrices

A. Matrix Materials

The matrix is formed by crosslinking ionically, covalently, or by combinations thereof precursor molecules to a polymeric network and/or by swelling one or more polymeric materials, i.e. matrices, to form a polymeric network having sufficient inter-polymer spacing to allow for in-growth or migration into the matrix of cells. In one embodiment the matrix is formed of proteins, preferably proteins naturally present in the patient into which the matrix is to be implanted. A particularly preferred matrix protein is fibrin, although matrices made from other proteins, such as collagen and gelatine can also be used. Polysaccharides and glycoproteins may also be used to form the matrix. It is also possible to use synthetic polymers which are crosslinkable by ionic or covalent binding.

Fibrin Matrices

Fibrin is a natural material which has been reported for several biomedical applications. Fibrin has been described as material for cell in-growth matrices in U.S. Pat. No. 6,331,422 to Hubbell et al. Fibrin gels have been used as sealants because of its ability to bind to many tissues and its natural role in wound healing. Some specific applications include use as a sealant for vascular graft attachment, heart valve attachment, bone positioning in fractures and tendon repair. Additionally, these gels have been used as drug delivery devices, and for neuronal regeneration. Although fibrin provides a solid support for tissue regeneration and cell in-growth, there are few active sequences in the monomer that directly enhance these processes.

The process by which fibrinogen is polymerized into fibrin has also been characterized. Initially, a protease cleaves the dimeric fibrinogen molecule at the two symmetric sites. There are several possible proteases than can cleave fibrinogen, including thrombin, peptidase, and protease III, and each one severs the protein at a different site. Once the fibrinogen is cleaved, a self-polymerization step occurs in which the fibrinogen monomers come together and form a non-covalently crosslinked polymer gel. This self-assembly happens because binding sites become exposed after protease cleavage occurs. Once they are exposed, these binding sites in the centre of the molecule can bind to other sites on the fibrinogen chains, which are present at the ends of the peptide chains. In this manner, a polymer network is formed. Factor XIIIa, a transglutaminase activated from Factor XIII by thrombin proteolysis, may then covalently crosslink the polymer network. Other transglutaminases exist and may also be involved in covalent crosslinking and grafting to the fibrin network.

Once a crosslinked fibrin gel is formed, the subsequent degradation is tightly controlled. One of the key molecules in controlling the degradation of fibrin is $\alpha$2-plasmin inhibitor. This molecule acts by crosslinking to the $\alpha$ chain of fibrin through the action of Factor XIIIa. By attaching itself to the gel, a high concentration of inhibitor can be localized to the gel. The inhibitor then acts by preventing the binding of plasminogen to fibrin and inactivating plasmin. The $\alpha$2-plasmin inhibitor contains a glutamine substrate. The exact sequence has been identified as NQEQVSPL (SEQ ID NO: 2), with the first glutamine being the active amino acid for crosslinking.

It has been demonstrated that bi-domain peptides, which contain a factor XIIIa substrate sequence and a bioactive peptide sequence, can be cross-linked into fibrin matrix and that this bioactive peptide retains its cellular activity in vitro.

Depending on the indication and substances mixed into the fibrin matrix the concentration of thrombin might vary. In one preferred embodiment, the fibrin matrix contains fibrinogen in a range of 5 to 65 mg per millilitre fibrin matrix, more preferably 15 to 60 mg per millilitre fibrin matrix, even more preferably from 25 to 55 mg per millilitre fibrin matrix, and most preferably 30 to 45 mg per millilitre fibrin matrix. Thrombin is present in a range of 0.5 to 5 I.U. per millilitre fibrin matrix, more preferably in a range of between 1.25 to 3.25 I.U. per millilitre fibrin matrix, most preferably from 1.5 to 2.5 I.U. per millilitre fibrin matrix. Additionally a calcium ion source helps to form the fibrin matrix. The calcium ion source is preferably $CaCl_2*2H_2O$ in a concentration of 0.5 to 5 mg per ml fibrin matrix, even more preferable of 2 to 3.5 mg per ml fibrin matrix, most preferably of 2.5 to 3 mg per ml fibrin matrix. I.U. stands for one international unit of thrombin and is defined as the activity contained in 0.0853 mg of the First International Standard of Human Thrombin. Supplemented fibrin matrices formed from materials present in these concentration ranges are preferably used for all the indications which do not require the addition of a contrast agent, like bone cysts and bone tumours.

When one or more contrast agents are present in the matrix, the amount of thrombin in the fibrin matrix is generally greater than the amount of thrombin in the same fibrin matrix in the absence of a contrast agent. Contrast agents are preferably added when the supplemented matrix is used as a prophylactic treatment to prevent fractures in osteoporotic bones, i.e. injection into the vertebra or femural neck. In these cases the fibrin matrix typically contains thrombin in a concentration range of between 7.5 to 125 I.U. thrombin per millilitre fibrin matrix, preferably in a range of between 25 to 50 I.U. thrombin per millilitre fibrin matrix and most preferred in a range of between 35 to 40 I.U. thrombin per millilitre fibrin matrix.

Precursor Solutions for Forming Fibrin Matrices

Preferably two precursor solutions are used to form a fibrin matrix. The first precursor solution contains fibrinogen, preferably 10 to 130 mg fibrinogen per millilitre precursor solution, more preferably 30 to 120 mg fibrinogen per millilitre precursor solution, even more preferably from 50 to 110 mg fibrinogen per millilitre precursor solution, and most preferably 60 to 90 mg fibrinogen per millilitre precursor solution. If thrombin has to be added to form the matrix and in those cases in which the indication requires one or more contrast agents, the second precursor solution contains thrombin, preferably 15 to 250 I.U. thrombin per millilitre precursor solution, more preferably 50 to 100 I.U. thrombin per millilitre precursor solution, and most preferably 70 to 80 I.U. thrombin per millilitre precursor solution. Additionally a calcium ion source may be present in at least one of the precursor solutions. The calcium ion source is preferably $CaCl_2*2H_2O$, preferably in a concentration of 1 to 10 mg per ml precursor solution, even more preferable of 4 to 7 mg per ml precursor solution, most preferably of 5 to 6 mg per ml precursor solution. Optionally, an enzyme capable of catalyzing the matrix formation, such as Factor XIIIa, is added to at least one precursor solution. Preferably, Factor XIIIa is present in a concentration of 0.5 to 100 I.U. per millilitre precursor solution, more preferably of 1 to 60 I.U. per millilitre precursor solution, and most preferably of 1 to 10 I.U. per millilitre precursor solution.

In cases in which the presence of a contrast agent is not required, the fibrin matrix is preferably formed from preferably two precursor solutions. The first precursor solution typically contains fibrinogen, preferably in a concentration range from 10 to 130 mg fibrinogen per millilitre precursor solution, more preferably from 30 to 120 mg fibrinogen per millilitre precursor solution, even more preferably from 50 to 110 mg fibrinogen per millilitre precursor solution, and most preferably from 60 to 90 mg fibrinogen per millilitre precursor solution. If thrombin has to be added to form the matrix, the second precursor solution contains thrombin, preferably in a concentration range from 1 to 10 I.U. thrombin per millilitre precursor solution, more preferably from 2.5 to 6.5 I.U. thrombin per millilitre precursor solution, most preferably from 3 to 5 I.U. thrombin per millilitre precursor solution. Additionally a calcium ion source is in one of the precursor solutions. The calcium ion source is preferably $CaCl_2*2H_2O$ in a concentration range from 1 to 10 mg per ml precursor solution, even more preferably from 4 to 7 mg per ml precursor solution, most preferably from 5 to 6 mg per ml precursor solution. Optionally, an enzyme capable of catalyzing the matrix formation, like Factor XIIIa, is added to a precursor solution. Preferably, Factor XIIIa is present in a concentration range from 0.5 to 100 I.U. per millilitre precursor solution, more preferably from 1 to 60 I.U. per millilitre precursor solution, and most preferably from 1 to 10 I.U. per millilitre precursor solution.

Synthetic Matrices and Precursor Solutions

Crosslinking reactions for forming synthetic matrices for application in the body include (i) free-radical polymerization between two or more precursors containing unsaturated double bonds, as described in Hem et al., *J. Biomed. Mater. Res.* 39:266-276 (1998), (ii) nucleophilic substitution reaction such as e.g. between a precursor including an amine group and a precursor including a succinimidyl group as disclosed in U.S. Pat. No. 5,874,500 to Rhee et al., (iii) condensation and addition reactions, and (iv) Michael type addition reactions between a strong nucleophile and a conjugated unsaturated group or bond (as a strong electrophile). Particularly preferred is the reaction between a precursor molecule having a thiol or amine group as the nucleophilic group and precursor molecules including acrylate or vinyl sulfone groups as electrophilic groups. The most preferred nucleophilic group is the thiol group. Michael type addition reactions are described in WO 00/44808 to Hubbell et al. Michael type addition reactions allow for in situ crosslinking of at least a first and a second precursor component under physiological conditions in a self-selective manner, even in the presence of sensitive biological materials. When one of the precursor components has a functionality of at least two, and at least one of the other precursor components has a functionality greater than two, the system will self-selectively react to form a cross-linked three dimensional matrix.

Preferably the conjugated unsaturated groups or conjugated unsaturated bonds are acrylates, vinylsulfones, methacrylates, acrylamides, methacrylamides, acrylonitriles, vinylsulfones, 2- or 4-vinylpyridinium, maleimides, or quinones.

The nucleophilic groups are preferably thiol-groups, amino-groups or hydroxyl-groups. Thiol groups are substantially more reactive than unprotonated amine groups. The pH is important in this consideration: the deprotonated thiol is substantially more reactive than the protonated thiol. Therefore, the addition reactions involving a conjugated unsaturation, such as an acrylate or a quinone, with a thiol to convert two precursor components into a matrix, will often be best carried out most quickly and self-selectively at a pH of approximately 8. At pH of approximately 8, most of the thiols of interest are deprotonated (and thus more reactive) and most of the amines of interest are still protonated (and thus less reactive). When a thiol is used as the first precursor molecule, a conjugate structure that is selective in its reactivity for the thiol relative to amines is highly desirable.

Suitable first and second precursor molecules include proteins, peptides, polyoxyalkylenes, poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-poly(propylene oxide) block copolymers. A particularly preferred precursor molecule is polyethylene glycol.

Polyethylene glycol (PEG) provides a convenient building block. One can readily purchase or synthesize linear (meaning with two ends) or branched (meaning more than two ends) PEGs and then functionalize the PEG end groups to introduce either a strong nucleophile, such as a thiol, or a conjugated structure, such as an acrylate or a vinylsulfone. When these components are either mixed with each other or with a corresponding component in a slightly basic environment, a matrix will be formed by reaction between the first and the second precursor component. A PEG component can be reacted with a non-PEG component, and the molecular weight or hydrophilicity of either component can be controlled to manipulate the mechanical characteristics, the permeability, and the water content of the resulting matrix.

In the formation of matrices, especially matrices that are desired to degrade in vivo, peptides provide a very convenient building block. It is straightforward to synthesize peptides that contain two or more cysteine residues, and this component can then readily serve as the first precursor component with nucleophilic groups. For example, a peptide with two free cysteine residues will readily form a matrix when mixed with a PEG tri-vinylsulfone (a PEG having three arms with vinylsulfones at each of its arms) at physiological or slightly higher pH (e.g., 8 to 9). The gelation can also proceed well at even higher pH, but at the potential expense of self-selectivity. When the two liquid precursor components are mixed together, they react over a period of a few minutes to form an elastic gel, consisting of a network of PEG chains, bearing the nodes of the network, with the peptides as connecting links. The peptides can be selected as protease substrates, so as to make the network capable of being infiltrated and degraded by cells, as is done in a protein-based network, such as in a fibrin matrix. Preferably the sequences in the domains are substrates for enzymes that are involved in cell migration (e.g., as substrates for enzymes such as collagenase, plasmin, metalloproteinase (MMP) or elastase), although suitable domains are not be limited to these sequences. One particularly useful sequence is a substrate for the enzyme plasmin. The degradation characteristics of the gels can be manipulated by changing the details of the peptide that serves as the cross-linking nodes. One may make a gel that is degradable by collagenase, but not plasmin, or by plasmin, but not collagenase. Furthermore, it is possible to make the gel degrade faster or slower in response to such an enzyme, simply by changing the amino acid sequence so as to alter the $K_m$ or $k_{cat}$, or both, of the enzymatic reaction. One can thus make a matrix that is biomimetic, in that it is capable of being remodeled by the normal remodeling characteristics of cells. For example, such a study shows substrate sites for the important protease plasmin. The gelation of the PEG with the peptide is self-selective.

Optionally, biofunctional agents can be incorporated into the matrix to provide chemical bonding to other species (e.g., a tissue surface). Having protease substrates incorporated into the matrix is important when the matrix is formed from PEG vinylsulfone. Other than matrices formed from the reaction of PEG acrylates and PEG thiols, matrices formed from PEG vinylsulfones and PEG thiols do not contain hydrolytically degradable bonds. Therefore, the incorporation of protease substrates allows the matrix to degrade in the body.

The synthetic matrices are operationally simple to form. Two liquid precursors are mixed; one precursor contains a precursor molecule with nucleophilic groups and the other precursor molecule contains the electrophilic groups. Physiological saline can serve as the solvent. Minimal heat is generated by reaction. Therefore, the gelation can be carried out in vivo or in vitro, in direct contact with tissue, without untoward toxicity. Thus polymers other than PEG may be used, either telechelically modified or modified on their side groups.

For most healing indications, the rate of cell in-growth or migration of cells into the matrix in combination with an adapted degradation rate of the matrix is crucial for the overall healing response. The potential of hydrolytically non-degradable matrices to become invaded by cells is primarily a function of network density. If the existing space between branching points or nodes is too small in relation to the size of the cells or if the rate of degradation of the matrix, which results in creating more space within the matrix, is too slow, a very limited healing response will be observed. Healing matrices found in nature, as e.g. fibrin matrices, which are formed as a response to injury in the body are known to consist of a very loose network which very easily can be invaded by cells. The infiltration is promoted by ligands for cell adhesion which are an integrated part of the fibrin network.

Matrices made from synthetic hydrophilic precursor molecules, like polyethylene glycol, swell in aqueous environment after formation of the polymeric network. In order to achieve a sufficiently short gelling time (between 3 to 10 minutes at a pH of between 7 to 8 and a temperature in a range of 36 to 38° C.) and quantitative reaction during in-situ formation of the matrix in the body, the starting concentration of the precursor molecules must be sufficiently high. Under such conditions, swelling after network formation would not take place, and the necessary starting concentrations would lead to matrices too dense for cell infiltration when the matrix is not degradable in aqueous environment. Thus swelling of the polymeric network is important to enlarge and widen the space between the branching points.

Irrespective of the starting concentration of the precursor molecules, hydrogels made from the same synthetic precursor molecules, such as a four arm PEG vinylsulfone and a peptide with SH groups, swell to the same water content in equilibrium state. This means that the higher the starting concentration of the precursor molecules are, the higher the end volume of the hydrogel is when it reaches its equilibrium state. If the space available in the body is too small to allow for sufficient swelling and in particular if the linkage formed from the precursor components are not hydrolytically degradable, the rate of cell infiltration and the healing response will decrease. As a consequence, the optimum between two contradictory requirements for application in the body must be found. Good cell infiltration and subsequent healing responses have been observed with a three-dimensional polymeric network formed from the reaction of a trifunctional branched polymer with at least three arms substantially similar in molecular weight and a second precursor molecule that is at least a bifunctional molecule. The ratio of equivalent weight of the functional groups of the first and second precursor molecules is between 0.9 and 1.1. The molecular weights of the arms of the first precursor molecule, the molecular weight of the second precursor molecule and the functionality of the branching points are selected such that the water content of the resulting polymeric network is between the equilibrium weight % and 92 weight % of the total weight of the polymeric network after completion of water uptake. Preferably the water content is between 93 and 95 weight % of the total weight of the polymeric network and the water after completion of water uptake. Completion of water uptake can be achieved either when the equilibrium concentration is reached or when the space available in the matrix does not allow for further volume increase. It is therefore preferred to choose the starting concentrations of the precursor components to be as low as possible. This is true for all swellable matrices but in particular for those matrices which undergo cell-mediated degradation and do not contain hydrolytically degradable linkages in the polymeric network.

The balance between gelling time and low starting concentration in particular for hydrolytically non-degradable gels should to be optimized based on the structure of the precursor molecules. In particular, the molecular weight of the arms of the first precursor molecule, the molecular weight of the second precursor molecule and the degree of branching, i.e. the functionality of the branching points, have to be adjusted accordingly. The actual reaction mechanism has a minor influence on this interplay.

If the first precursor molecule is a three or four arm polymer with a functional group at the end of each arm and the second precursor molecule is a linear bifunctional molecule, preferably a peptide containing at least two cysteine groups, then the molecular weight of the arms of the first precursor molecule and the molecular weight of the second precursor molecule are preferably chosen such that the links between the branching points after formation of the network have a molecular weight in the range of between 10 to 13 kDa (under the conditions that the links are linear, not branched), preferably between 11 and 12 kDa. This allows for a starting concentration of the sum of first and second precursor molecules in a range of between 8 to 12 weight %, preferably between 9 and 10 weight % of the total weight of the first and second precursor molecule in solution (before network formation). In case the branching degree of the first precursor component is increased to eight and the second precursor molecule is still a linear bifunctional molecule, the molecular weight of the links between the branching points is preferably increased to a molecular weight of between 18 to 24 kDa. When the branching degree of the second precursor molecule is increased from a linear to a three or four arm precursor component, the molecular weight, i.e. the length of the links increase accordingly. In a preferred embodiment a composition is chosen including as the first precursor molecule a trifunctional three arm 15 kD polymer, i.e. each arm having a molecular weight of 5 kD and as the second precursor molecule a bifunctional linear molecule of a molecular weight in the range of between 0.5 to 1.5 kD, even more preferably around 1 kD. Preferably the first and the second precursor component is a polyethylene glycol.

In a preferred embodiment the first precursor component includes as functional groups conjugated unsaturated groups or bonds, most preferred an acrylate or a vinylsulfone and the functional groups of the second precursor molecule includes a nucleophilic group, preferably a thiol or amino groups. In another preferred embodiment of the present invention the first precursor molecule is a four arm 15 to 20 kD polymer, preferably 15 kD polymer, having functional groups at the terminus of each arm and the second precursor molecule is a bifunctional linear molecule of a molecular weight in the range of between 3 and 4 kDa, preferred between 3.4 kDa. Preferably the first precursor molecule is a polyethylene glycol having acrylate groups and the second precursor molecule is a polyethylenglycol having thiol groups. In both preferred embodiments the starting concentration of the sum of first and second precursor molecule ranges from the 8 to 11 weight %, preferably between 9 and 10 weight % of the total weight of the first and second precursor molecule and water (before formation of polymeric network), preferably between 5 and 8 weight % to achieve a gelling time of below 10 minutes. These compositions have a gelling time at pH 8.0 and 37° C. of about 3-10 minutes after mixing.

When the matrix contains hydrolytically degradable linkages, formed e.g. by the preferred reaction between acrylates and thiols, the network density with regard to cell infiltration is especially important in the beginning, but in aqueous environment the linkages will be hydrolyzed and the network will be loosened, to allow for cell infiltration. With an increase in the overall branching degree of the polymeric network the molecular weight of the interlinks, i.e. the length of the links must increase.

B. Cell Attachment Sites

Cells interact with their environment through protein-protein, protein-oligosaccharide and protein-polysaccharide interactions at the cell surface. Extracellular matrix proteins provide a host of bioactive signals to the cell. This dense network is required to support the cells, and many proteins in the matrix have been shown to control cell adhesion, spreading, migration and differentiation. Some of the specific proteins that have been shown to be particularly active include laminin, vitronectin, fibronectin, fibrin, fibrinogen and collagen. Many studies of laminin have been conducted, and it has been shown that laminin plays a vital role in the development and regeneration of nerves in vivo and nerve cells in vitro, as well as in angiogenesis. Some of the specific sequences that directly interact with cellular receptors and cause either adhesion, spreading or signal transduction have been identified.

Laminin, a large multidomain protein, has been shown to consist of three chains with several receptor-binding domains. These receptor-binding domains include the YIGSR (SEQ ID NO: 1) sequence of the laminin B1 chain, LRGDN (SEQ ID NO: 3) of the laminin A chain and PDGSR (SEQ ID NO: 4) of the laminin B1 chain. Several other recognition sequences for cells have been identified. These include IKVAV (SEQ ID NO: 5) of the laminin A chain, and the sequence RNIAEIIKDI (SEQ ID NO: 6) of the laminin B2 chain. Particularly preferred is the RGD sequence from fibronectin In a further preferred embodiment peptide sites for cell adhesion are incorporated into the matrix, namely peptides that bind to adhesion-promoting receptors on the surfaces of cells. Such adhesion promoting peptides include those described above. Particularly preferred are the RGD sequence from fibronectin, the YIGSR (SEQ ID NO: 1) sequence from laminin. Incorporation of cell attachment sites is particularly preferred with synthetic matrices. However, cell attachment sites can also be included with some of the natural matrices. The incorporation can be accomplished, for example, by mixing a cysteine-containing cell attachment peptide with the precursor molecule including the conjugated unsaturated group, such as PEG acrylate, PEG acrylamide or PEG vinylsulfone. This step may occur shortly, e.g. a few minutes, before mixing with the remainder of the precursor component including the nucleophilic group, such as thiol-containing precursor component. If the cell attachment site does not include a cysteine, it can be chemically synthesized to include one. During this step, the adhesion-promoting peptide will become incorporated into one end of the precursor multiply functionalized with a conjugated unsaturation; when the remaining multi-thiol is added to the system, a cross-linked network will form.

The concentration of adhesion sites covalently bound into the matrix can influences the rate of cell infiltration. For example, for a given hydrogel, a RGD concentration range can be incorporated into the matrix with supports cell in-growth and cell migration in an optimal way. The optimal concentration range of adhesion sites like RGD is between 0.04 and 0.05 mM and even more preferably 0.05 mM in particular for a matrix having a water content between equilibrium concentration and 92 weight % after termination of water uptake.

A preferred embodiment is a supplemented matrix containing a bioactive factor, a four arm polyethylene glycol with a molecular weight of about 20,000 Da crosslinked with a protease degradation site GCRPQGIWGQDRC (SEQ ID NO: 7) and 0.050 mM RGD; this matrix demonstrates particularly good cell in-growth results and healing of bone defects. Preferably the matrix contains PTH 1-34 covalently bound to the matrix. The starting concentration of PEG and peptide is below 10 weight % of the total weight of the molecules and water (before swelling). The gels have a useable consistency and allow the osteoblasts and precursor cell to easily infiltrate the matrix.

C. Bioactive Factors

Bioactive factors are the active ingredients for the treatment of the specific bone defects areas of non-healthy bone, e.g. osteoporosis and bone cysts. It has been surprisingly found that specific bioactive factors, i.e. PTH and BMP, in particular $PTH_{1-34}$, BMP2 and BMP 7 are suitable for local treatment of osteoporotic bones and bone areas as well as areas of bone cysts and bone tumours. In the past, these bone factors have been explored for systemic treatment. However, there was no suggestion that they may be useful active ingredients of locally applied formulations, insofar as the treatment of the bone defects are concerned. It has been found that when these bioactive factors are incorporated into an injectable matrix formulation and injected into specific bone defects areas of non-healthy bone they increase the bone density in that bone area. Preferably the bioactive factor is covalently attached to the above-described matrices, thus ensuring a controlled release of the bioactive factors. The bioactive factor may be in the form of a fusion peptide, which contains the bioactive factor in a first domain and a covalently crosslinkable substrate domain in a second domain. Optionally, a degradation site is located between the first and second domains.

a. PTH

The term "PTH" as used herein includes the human sequence of $PTH_{1-84}$ and all truncated, modified and allelic versions of PTH which exhibit bone formation properties when covalently bound to biodegradable natural or synthetic matrices. Preferred truncated versions of PTH are $PTH_{1-38}$, $PTH_{1-34}$, $PTH_{1-31}$, $PTH_{1-28}$ or $PTH_{1-25}$. Most preferred is PTH$_{1-34}$. Preferably, the PTH is human PTH, although PTH from other sources, such as bovine PTH, may be suitable.

b. BMP

The bone morphogenetic protein can be any of the known BMPs or any modified or allelic version of BMP exhibiting bone forming properties. Particularly preferred are BMP 2 and BMP 7.

BMP 2

The term "BMP 2" as used herein includes the human sequence of BMP $2_{1-396}$ and all truncated, modified and allelic versions of BMP 2 which exhibit similar biological activity when covalently bound to biodegradable natural or synthetic matrices. A preferred truncated version of BMP 2 is BMP $2_{283-396}$. Preferably, the BMP 2 is human BMP 2, although BMP 2 from other sources may be suitable, in particular from mouse or rat in view of a 100% identity of the amino acid sequences of BMP 2 from humans, mice or rats.

BMP 7

The term "BMP 7" as used herein includes the human sequence of BMP $7_{1-431}$ and all truncated, modified and allelic versions of BMP 7 which exhibit similar biological activity when covalently bound to biodegradable natural or synthetic matrices. A preferred truncated version of BMP 7 is BMP $7_{293-431}$. Preferably, the BMP 7 is human BMP 7, although BMP 7 from other sources may be suitable, in particular from mouse in view of a 98% identity of the amino acid sequences of BMP 7 from humans and mice.

c. Fusion Peptides

Crosslinkable Substrate Domains

The fusion peptides comprise at least two domains wherein the first domain comprises the bioactive factor and the second domain comprises a substrate domain crosslinkable to the matrix before, during or after its formation. The substrate domain can be a domain for an enzyme, preferably a substrate domain for a transglutaminase ("transglutaminase substrate domain"), more preferably for a tissue transglutaminase ("tissue transglutaminase substrate domain"), and most preferably it is a substrate domain for Factor XIIIa ("Factor XIIIa substrate domain"). Transglutaminases catalyse acyl-transfer reactions between the gamma-carboxamide group of protein bound glutaminyl residues and the epsilon-amino group of lysine residues, resulting in the formation of N-epsilon-(gamma-glutamyl)lysine isopeptide side chains bridges. The amino acid sequence of the fusion peptide can be designed to further contain an enzymatic or hydrolytic cleavage site, thus that the bioactive factor can be released with little or no modification to the primary structure. Transglutaminase substrate domains and in particular, Factor XIIIa substrate domains are suitable to link the fusion peptide to fibrin matrices but also to synthetic matrices in case pending primary amino groups are present at the synthetic molecule. When used with a fibrin matrix the degradation site in the fusion peptide is preferably enzymatically degradable, so that the release of the PTH is controlled by cell specific processes, such as localized proteolysis.

The crosslinkable substrate domain may include GAKDV (SEQ ID NO: 8), KKKK (SEQ ID NO: 9), YRGDTIGEGQQHHLGG (SEQ ID NO: 10), or NQEQVSPL (SEQ ID NO: 2).

The most preferred Factor XIIIa substrate domain has an amino acid sequence of NQEQVSPL (SEQ ID NO: 2) and is herein referred to as "TG" and TG-PTH.

The PTH fusion peptide may be produced recombinantly or by chemical synthesis. The PTH 1-34 fusion peptide is preferably produced by chemical synthesis. The BMP fusion peptide is produced recombinantly preferably by bacterial processes.

For the incorporation of PTH, BMP 2 or BMP 7 into a matrix formed from synthetic precursor components, the PTH or BMP fusion peptide or any other peptide can be also incorporated when synthesized with at least one additional cysteine group (—SH) preferably at the N terminus of PTH$_{1-34}$, BMP 2 or BMP 7 as the crosslinkable substrate domain. The cysteine can be either directly attached to the PTH$_{1-34}$, BMP 2 or BMP 7 or through a linker sequence. The linker sequence can additionally include an enzymatically or hydrolytically degradable amino acid sequence, so that the PTH, BMP 2 or BMP 7 can be cleaved from the matrix by enzymes in substantially the native form. The free cysteine group reacts with the conjugated unsaturated group of the precursor component in a Michael type addition reaction. The thiol group of the cysteine can react with a conjugated unsaturated bond on the synthetic polymer to form a covalent linkage.

These sites may be degradable either by non-specific hydrolysis (i.e. an ester bond) or they may be substrates for specific enzymatic (either proteolytic or polysaccharide degrading) degradation.

The degradation sites allow the PTH, BMP 2 or BMP 7 to be released with little or no modification to the primary peptide sequence, which may result in higher activity of the factor. In addition, it allows the release of the factor to be controlled by cell specific processes. This allows factors to be released at different rates within the same material depending on the location of cells within the material. This also reduces the amount of total PTH$_{1-34}$, BMP 2 or BMP 7 needed, since its release is controlled by cellular processes. In one possible explanation for the strong healing of the above mentioned bone defects with PTH incorporated and preferably bound to a matrix, it is deemed important that the PTH is administered locally over an extended period of time (i.e. not just a single pulsed dose) but not in a continuous fashion. This is accomplished by a slow degradation, through either enzymatic cleavage or hydrolytic cleavage of the matrix. In this way, the molecule is then delivered through a pseudo-pulsed effect that occurs over a sustained period of time. When a preosteoblastic cell infiltrates the matrix, it will encounter a PTH molecule which will induce further proliferation of the preosteoblast as well as synthesis of multiple growth factors crucial for new bone formation. However, if that particular cell does not continue to liberate bound PTH from the matrix, it will not begin to produce interleukin-6, thereby avoiding the later stage catabolic effects on osteoclasts formation. The net result is then higher bone mineral density and net formation of bone matrix. Finally, the therapeutic effects of the peptide are localized to the defect region and are subsequently magnified.

Degradation Sites of the Fusion Peptide

An enzymatic or hydrolytic degradation site can be present between the first and the second domains of the fusion peptide. The degradation sites may be degradable by specific enzymatic degradation. Preferably the degradation site is cleavable by an enzyme selected from the group consisting of plasmin and matrix metalloproteinase. By careful selection of $K_m$ and $k_{cat}$ of this enzymatic degradation site, degradation could be controlled to occur either before or after the matrix formation and/or by utilizing similar or dissimilar enzymes to degrade the matrix. These degradable sites allow the engineering of more specific release of bioactive factors from matrices. The degradable site can be cleaved by enzymes released from cells which invaded the matrix. The degradation site allows the rate of delivery to be varied at different locations within the matrix depending on cellular activity at that location and/or within the matrix. Additional benefits include the lower total drug dose within the delivery system, and spatial regulation of release which permits a greater percentage of the drug to be released at the time of greatest cellular activity. The degradation site is abbreviated herein as "pl".

Proteolytically degradable sites could include substrates for collagenase, plasmin, elastase, stromelysin, or plasminogen activators. Exemplary substrates are listed below. N1-N5 denote amino acids 1-5 positions toward the amino terminus of the protein from the site were proteolysis occurs. N1'-N4' denote amino acids 1-4 positions toward the carboxy terminus of the protein from the site where proteolysis occurs.

TABLE 1

Sample substrate sequences for protease

| Protease | N5 | N4 | N3 | N2 | N1 | N1' | N2' | N3' | N4' | SEQ ID NO |
|---|---|---|---|---|---|---|---|---|---|---|
| Plasmin[1] | | | | L | I | K | M | K | P | | SEQ ID NO: 11 |
| Plasmin[1] | | | | N | F | K | S | Q | L | | SEQ ID NO: 12 |
| Stromelysin[2] | Ac | G | P | L | A | L | T | A | L | SEQ ID NO: 13 |
| Stromelysin[2] | | Ac | P | F | E | L | R | A | $NH_2$ | SEQ ID NO: 14 |
| Elastase[3] | | | Z- | A | A | F | A | $NH_2$ | | SEQ ID NO: 15 |
| Collagenase[4] | | G | P | L | G | I | A | G | P | SEQ ID NO: 16 |
| t-PA[5] | P | H | Y | G | R | S | G | G | | SEQ ID NO: 17 |
| u-PA[5] | P | G | S | G | R | S | A | S | G | SEQ ID NO: 18 |

Reference:
[1]Takagi and Doolittle, (1975) Biochem. 14: 5149–5156.
[2]Smith et al., (1995). J. Biol. Chem. 270: 6440–6449.
[3]Besson et al., (1996) Analytical Biochemistry 237: 216–223.
[4]Netzel-Arnett et al., (1991) J. Biol. Chem.. 266: 6747–6755.
[5]Coombs et al., 1998. J. Biol. Chem. 273: 4323–4328

REFERENCE

1 Takagi and Doolittle, (1975) *Biochem.* 14:5149-5156.
2. Smith et al., (1995). *J. Biol. Chem.* 270:6440-6449.
3. Besson et al., (1666) *Analytical Biochemistry* 237:216-223.
4. Netzel-Arnett et al., (1991) *J. Biol. Chem.* 266:6747-6755.
5. Coombs et al., 1998. *J. Biol. Chem.* 273:4323-4328

In a preferred embodiment, the sequence YKNR (SEQ. NO: 19) is located between the first domain and the second domain and makes the linkage plasmin degradable.

A particular preferred PTH fusion peptide is TGplPTH: NQEQVSPLYKNRSVSEIQLM-HNLGKHLNSMERVEWLRKKLQDVHNF (SEQ ID NO: 20)

Enzymes that could be used for proteolytic degradation are numerous. Proteolytically degradable sites could include substrates for collagenase, plasmin, elastase, stromelysin, or plasminogen activators.

In another preferred embodiment an oligo-ester domain could be inserted between the first and the second domain. This can be accomplished using an oligo-ester such as oligomers of lactic acid.

Design of Fusion Proteins for Incorporation

Preferred fusion proteins include:

TG-PTH$_{1-34}$: This is a modified form of PTH comprising the amino acids 1-34 of the native PTH as well as a TG (transglutaminase) substrate domain: NQEQVSPLSVSEIQLM-HNLGKHLNSMERVEWLRKKLQDVHNF (SEQ ID NO: 21)

TG-pl-PTH$_{1-34}$: This form corresponds to TG-PTH except that it additionally contains a plasmin-degradable sequence (pl) between the TG sequence and the PTH$_{1-34}$: NQEQVSPLYKNRSVSEIQLM-HNLGKHLNSMERVEWLRKKLQDVHNF (SEQ ID NO: 20)

TG-BMP 2$_{283-396}$: This is a modified form of BMP 2 comprising the amino acids 283-396 of the native PTH as well as a TG (transglutaminase) substrate domain:
Met-Asn-Gln-Glu-Gln-Val-Ser-Pro-Leu-Pro-Val-Glu-Leu-Pro-Leu-Ile-Lys-Met-Lys-Pro-His-BMP 2$_{283-396}$ (SEQ ID NO: 22).

Combination of Matrices or Precursor Components and Bioactive Factors

In a preferred embodiment the supplemented synthetic or fibrin matrix (respectively its precursor solutions) comprises the matrix and PTH or PTH fusion peptide, preferably in a concentration range of between 0.01 and 2 mg PTH or PTH fusion peptide/mL matrix or precursor components forming the matrix, preferably of between 0.02 to 1.0 mg PTH or PTH fusion peptide/mL matrix or precursor components forming the matrix, more preferably of between 0.03 and 0.5 mg PTH or PTH fusion peptide/mL matrix or precursor components forming the matrix and most preferably in a range of between 0.05 to 0.2 mg PTH or PTH fusion peptide/mL of matrix or precursor components forming the matrix. Depending on the age of the patient, certain subranges of the PTH concentration or PTH fusion peptide concentration are preferred. If the supplemented matrix is applied to treat bone cysts in children, the concentration of PTH or PTH fusion peptide is preferably in a range of between 0.01 and 0.35 mg PTH or PTH fusion peptide/mL matrix or precursor components forming the matrix and most preferably in a concentration range of between 0.05 and 0.15 mg PTH or PTH fusion peptide/mL matrix or precursor components forming the matrix. Whereas if the formulation is applied to locally increase the bone density of osteoporotic bone in adults, the preferred concentration of PTH or PTH fusion peptide is in a range of between 0.5 and 2 mg PTH or PTH fusion peptide/mL matrix or precursor components forming the matrix, more preferably between 0.7 and 1.5 mg PTH or PTH fusion peptide/mL matrix or precursor components and most preferably between 0.9 and 1.1 mg PTH or PTH fusion peptide/mL matrix or precursor components forming the matrix. In a preferred embodiment the matrix is a fibrin matrix.

II. Methods for Incorporation and/or Release of Bioactive Factors

In one preferred embodiment for incorporation of a bioactive factor, like PTH, or BMP or a fusion peptide within the matrix, the bioactive factor will be incorporated, physically or chemically within the matrix during its gelation. In case of a fibrin matrix, Factor XIIIa is a transglutaminase that is active during coagulation to fibrin. This enzyme, formed naturally from factor XIII by cleavage by thrombin or additionally added to the fibrin precursor solutions if higher concentrations are required, functions to attach fibrin chains to each other via amide linkages, formed between glutamine side chains and lysine side chains. The enzyme also functions to attach other peptides to fibrin during coagulation. Specifically the sequence NQEQVSPL (SEQ ID NO: 2), has been demonstrated to function as an effective substrate for Factor XIIIa. In case of synthetic matrices the fusion peptide should be a functional group being able to react with a functional group of the precursor components forming the synthetic matrix under physiological conditions in the body. For example if the precursor molecule contains acrylate groups the fusion peptide should contain free thiol groups which react with the acrylate group in a Michael type addition reaction. Depending of the nature of the bioactive factor mixing of an unmodified factor is also possible to achieve a sustained release from the matrix.

III. Methods of Application

The supplemented matrices may be formed in situ at the desired location upon injection of the separated precursor components, or may be preformed and then implanted into the desired location. Depending on the indication the supplemented matrices are applied or injected at different stages of gelation. If the matrix is injected into bone cysts, it is preferably applied right after mixing of the precursor solutions, i.e. in a still liquid state. If the injection of the supplemented matrix is in areas of non-healthy bones which are affected by osteoporosis, they are preferably injected in a pre-gelled state. The precursor solutions are mixed and after gelation (usually after about 30 sec to 2 min) the gel is injected through a thick needle into the affected area in the bone. This is done to prevent leakage of a still liquid matrix into the blood circulation.

For some of the indications there might be the desire to see distribution of the material in the bone area to which it is applied during injection. In a preferred embodiment, an X-ray contrast agent, preferably one that is soluble in the matrix material, is added to the matrix precursor material.

Generally, contrast agents are classified as ionic and non-ionic contrast agents. Non-ionic contrast agents are preferred, although ionic contrast agents may also be used. Iodine-containing X-ray contrast agents are preferred.

Preferred non-ionic contrast agents include iodixanol, iohexol, iopamidol, iopentol, iopromide, iorneprol, iosimide, iotasul, iotrolan, ioversol, ioxilan, and metrizamide. The most preferred non-ionic contrast agent is Iohexol (CAS No. 66108-95-0). If iohexol is added to visualise the gel under fluoroscopy or X-ray, the matrix preferably contains 100 to 600 mg per millilitre of the matrix or precursor solutions that form the matrix, more preferably 250 to 500 mg per millilitre of the matrix or the precursor components forming the matrix, most preferably 300 to 450 mg per millilitre in the matrix or the precursor components forming the matrix.

Preferred ionic contrast agents include diatrizoate, iobenzamate, iocarmate, iocetamate, iodamide, iodipamide, iodoxamate, ioglicate, ioglycamate, iopanoate, iophendylate, iopronate, ioserate, iothalamate, iotroxate, ioxaglate, ioxithalamate, and metrizoate.

Contrast agents are commercially available and can be readily synthesized, as is well-known to the man skilled in the art.

Monitoring of the contrast agents may be accomplished with the methods generally used in the art, for example by X-ray, magnetic resonance imaging (MRI) or ultrasound imaging. It is well-known that contrast agents function by either modifying the X-ray absorption characteristics of the body sites in which they are distributed, by modifying the relaxation times of the water protons and thus are observable via magnetic resonance imaging, or by modifying the speed of sound or density in the body sites in which they are distributed. According to the present invention, it is preferred to use contrast agents which can be monitored by X-ray imaging.

As described herein, the supplemented matrix formulation injected into the body at different stages of gelation can gel in situ in or on the body. In another embodiment the supplemented matrix can be formed outside the body and then applied in the preformed shape. Irrespective of the kind of precursor component used, the precursor components should be separated prior to application of the mixture to the body to prevent combination or contact with each other under conditions that allow polymerization or gelation of the components. To prevent contact prior to administration, a kit which separates the compositions from each other may be used. Upon mixing under conditions that allow polymerization, the compositions form a bioactive factor supplemented three dimensional network. Depending on the precursor components and their concentrations, gelling can occur quasi-instantaneously after mixing.

In one embodiment the matrix is formed from fibrinogen. Fibrinogen, through a cascade of various reactions gels to form a matrix, when brought in contact with thrombin and a calcium source at appropriate temperature and pH. The three components, fibrinogen, thrombin, and the calcium source, should be stored separately. However, as long as at least one of the three components is kept separate, the other two components can be combined prior to administration.

In one embodiment, fibrinogen is dissolved (which may contain additionally aprotinin to increase stability) in a buffer solution at physiological pH (in a range from pH 6.5 to 8.0, preferably from pH 7.0 to 7.5) to form a first precursor solution and is stored separately from a solution of thrombin in a calcium chloride buffer (e.g. concentration range of from 40 to 50 mM). The buffer solution for the fibrinogen can be a histidine buffer solution at a preferred concentration of 50 mM including additionally NaCl at a preferred concentration of 150 mM or TRIS buffer saline (preferably at a concentration of 33 mM).

In a preferred embodiment, a kit contains a fusion protein, fibrinogen, thrombin, and a calcium source. Optionally, the kit may contain a crosslinking enzyme, such as Factor XIIIa. The fusion protein contains a bioactive factor, a substrate domain for a crosslinking enzyme and, optionally, a degradation site between the substrate domain and bioactive factor. The fusion protein may be present in either the fibrinogen or the thrombin precursor solution. In a preferred embodiment the fibrinogen precursor solution contains the fusion protein.

The solutions are preferably mixed by a two way syringe device, in which mixing occurs by squeezing the contents of both syringes through a mixing chamber and/or needle and/or static mixer.

In a preferred embodiment, both fibrinogen and thrombin are stored separately in lyophilised form. Either of the two can contain the bioactive factor, which is preferably a fusion protein. Prior to use, the tris or histidine buffer is added to the fibrinogen, the buffer may additionally contain aprotinin. The lyophilized thrombin is dissolved in the calcium chloride solution. Subsequently, the fibrinogen and the thrombin solutions are placed in separate containers/vials/syringe bodies and mixed by a two way connecting device, such as a two-way syringe. Optionally, the containers/vials/syringe bodies are bipartited thus having two chambers separated by an adjustable partition which is perpendicular to the syringe body wall. One of the chambers contains the lyophilised fibrinogen or thrombin, while the other chamber contains an appropriate buffer solution. When the plunger is pressed down, the partition moves and releases the buffer into the fibrinogen chamber to dissolve the fibrinogen. Once both fibrinogen and thrombin are dissolved, both bipartite syringe bodies are attached to a two-way connecting device and the contents are mixed by squeezing them through the injection needle attached to the connecting device. Optionally, the connecting device contains a static mixer to improve mixing of the contents.

In a preferred embodiment the fibrinogen is diluted eight fold and thrombin is diluted 20 fold prior to mixing. This ratio results in a gelation time of approximately one minute.

In another preferred embodiment, the supplemented matrix is formed from synthetic precursor components capable of undergoing a Michael addition reaction. Since the nucleophilic precursor component (the multi-thiol) only reacts with the multi-acceptor component (the conjugated unsaturated group) at basic pH, the three components which have to be stored separately prior to mixing are: the base, the nucleophilic component and the multi-acceptor component. Both the multi-acceptor and the multi-thiol component are stored as solutions in buffers. Both of the compositions can include the cell attachment site and additionally the bioactive molecule. Thus, the first composition of the system can for example include the solution of the nucleophilic component and the second composition of the system can include the solution of the multi-acceptor component. Either or both of the two compositions can include the base. In another embodiment, the multi-acceptor and the multi-thiol can be included as solution in the first composition and the second composition can include the base. Connecting and mixing occurs in the same way as previously described for fibrinogen. The bipartite syringe body is equally suitable for the synthetic precursor components. Instead of fibrinogen and thrombin the multi-acceptor and multi-thiol components are stored in pulverized form in one of the chamber and the other chamber contains the basic buffer.

Additionally, other components beside the above mentioned ingredients may be incorporated into the systems of the present invention, For example, a material containing a calcium mineral, i.e. a naturally occurring homogenous substance containing calcium ions such as hydroxyapatite, may be used.

While the compositions and methods have been described in terms of preferred embodiments, it will be apparent to those of skill in the art that variations may be applied to the composition, methods and in the steps or in the sequence of steps of the method described herein without departing from the concept, spirit and scope of the invention.

EXAMPLES

Example 1

Bioactivity of $PTH_{1-34}$ and $TGplPTH_{1-34}$ $PTH_{1-34}$-peptide showing similar activity to the full length $PTH_{1-84}$, and proteins of this length can be synthesized by standard solid state peptide synthesis methods.

All peptides were synthesized on solid resin using an automated peptide synthesizer using standard 9-fluorenylmethyloxycarbonyl chemistry. Peptides were purified by c18 chromatography and analyzed using reverse phase chromatography via HPLC to determine purity as well as mass spectroscopy (MALDI) to identify the molecular weight of each product. Using this method, $PTH_{1-34}$ as well as, TG-pl-$PTH_{1-34}$ (NQEQVSPLYKNRSVSEIQLM-HNLGKHLNSMERVEWLRKKLQDVHNF (SEQ ID NO: 20)) and $TGPTH_{1-34}$ (NQEQVSPLSVSEIQLM-HNLGKHLNSMERVEWLRKKLQDVHNF (SEQ ID NO: 21)) were synthesized. $TGplPTH_{1-34}$ and $TGPTH_{1-34}$ differs from $PTH_{1-34}$ in that it additionally comprises the Factor XIIIa substrate domain which is linked to $PTH_{1-34}$ via the plasmin degradable pl-sequence YKNR (SEQ ID NO: 19) in case of $TGplPTH_{1-34}$ and directly in case of $TGPTH_{1-34}$.

To study the bioactivity of the PTH fusion peptides, a reporter gene assay was established. In this assay, a plasmid that contains luciferase reporter gene which is linked to the promoter for the parathyroid hormone receptor is transfected into cells. Then, if the cell is exposed to PTH and the PTH subsequently binds to its receptor on the cell, a signal cascade, directed through elevated cAMP levels, is initiated. Through a natural feedback regulation, this then leads to a reduction of PTH receptor levels. As the reduction is directed through the promoter, it also then leads to a decrease in production of the linked reporter gene. Using this assay, the activity of both native $PTH_{1-34}$ as well as TG-pl-PTH1-34 were studied and compared to an international standard. It was observed that both of these molecules showed a similar level of activity, as the reduction in reporter gene expression for both was the same, and this level of activity was the same as for the international standard. The results are shown in FIG. 1.

Example 2

PTH Release from a Fibrin Matrix

A fibrin matrix was made from TISSEEL® Kit (Baxter AG, CH-8604 Volketswil/ZH) fibrin precursor components. The composition is listed in Table 2. In the presence of 0.1 µg/ml of $PTH_{1-34}$ or $TGPTH_{1-34}$ was then added to the thrombin, and mixed to form a homogenous concentration. $TGPTH_{1-34}$ only has a transglutaminase sequence at the amino terminus, without a degradation site. Thus, $TGPTH_{1-34}$ can only be liberated by degradation of the fibrin matrix itself. This peptide was synthesized as described above in Example 1.

For the first release assay, a fibrin matrix of 50 µl with 0.1 mg PTH or TGPTH per ml fibrin matrix was incubated at 37° C. in 10 ml buffer. Therefore, the concentration of PTH or TGPTH in the buffer in case of a total release would be 0.5 µg PTH or TGPTH/mL fibrin matrix. In order to compare the stability of PTH or TGPTH during the assay, samples of PTH or TGPTH were diluted directly in the buffer to a concentration of 0.5 µg PTH or TGPTH/mL fibrin matrix. Different buffers were tested: distilled water, phosphate buffer saline, tris-buffer saline.

Aliquots were taken at days 0, 1, 2, 4 and 6 and analysed by direct ELISA. The results showed that the PTH was not stable for more than 2 days in any of the buffers. Therefore, no conclusion could be made on the release data. The PTH stability was certainly affected by its low concentration and the buffers that were not optimal.

The release experiment was repeated by using a stabilizing buffer containing 50 mM mannitol in a 10 mM sodium acetate buffer. In addition, the buffer was exchanged every 2 days in order to prevent any degradation of peptide. The concentration of PTH or TGPTH was increased to 1 mg PTH or TGPTH/mL fibrin matrix in a 100 µl fibrin matrix and the incubation was achieved in 1 ml buffer. The concentration of PTH or TGPTH in the buffer in case of a total release would be 100 µg/mL fibrin matrix (200 times more than before). As in the first experiment, spiked samples (same amount of PTH or TGPTH dissolved in the buffer as control) were prepared to evaluate the stability of PTH or TGPTH during the experiment (100 µg/ml). Samples were collected every 2 to 4 days (with a change of buffer) during 2 weeks and analysed by direct ELISA. Spiked samples were also collected every 2 days. The results showed that under these conditions PTH and TGPTH are stable over 2 weeks.

Figure 2:
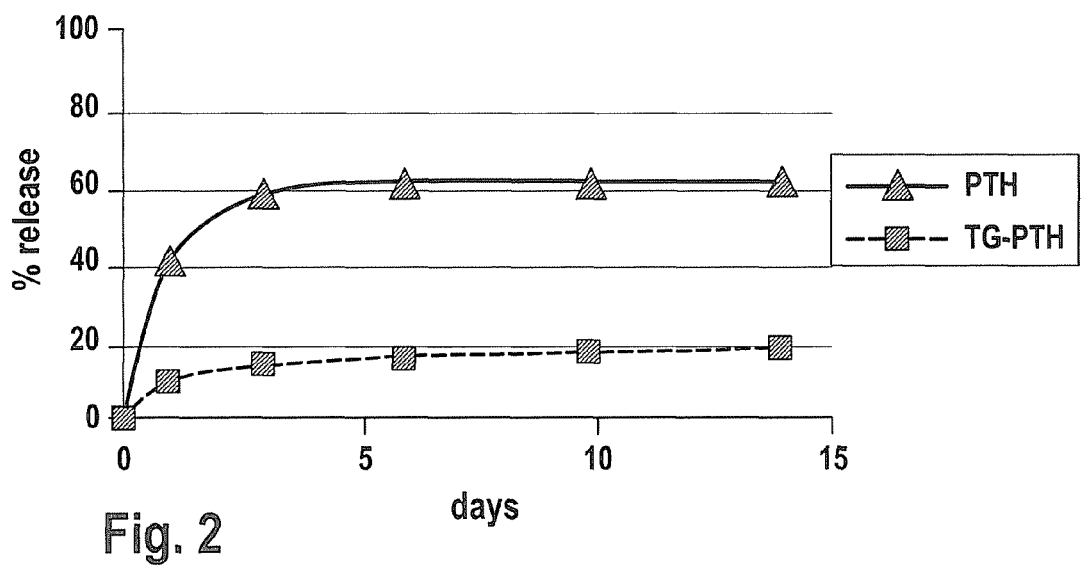
FIG. 2 shows the results of a PTH release assay from a fibrin matrix.

As can be seen from FIG. 2, the major release from the fibrin matrix is achieved within 3 days. Almost 60% of PTH and 13% of TGPTH were released after day 3. These data demonstrate the retention of PTH in the fibrin matrix is highly enhanced by addition of the TG sequence.

Example 3

Synthesis of a Supplemented Fibrin Matrix Comprising a PTH Fusion Peptide

The fibrin matrix was formed starting from the TISSEEL® Kit (Baxter AG, CH-8604 Volketswil/ZH) giving 4 mL fibrin matrix. TISSEEL® was produced from human derived pooled plasma and the content of active ingredients may vary from lot to lot within predefined ranges. Table 2 lists the final composition used.

TABLE 2

Final Composition comprising TISSEEL ® and active component

| Ingredients | Dose per 2 mL gel |
| --- | --- |
| Syringe 1 (1 mL) | |
| Active Component: | 0.2 to 20 mg |
| PTH$_{1-34}$ fusion peptide (TGplPTH$_{1-34}$) | |
| Clotting Agents | |
| Fibrinogen (Human) | 66-100 mg |
| Other Proteins | |
| Aprotinin (Bovine) | 2046-3409 KIU |
| Human Albumin | 9.1-18.2 mg |
| Buffer Components | |
| Niacinamide | 2.7-8.2 mg |
| L-Histidine | 9.1-22.7 mg |
| Sodium Citrate | 4.4-8.8 mg |
| Polysorbate 80 | 0.6-1.7 mg |
| Water for Injection | to 1 mL |
| Syringe 2 (1 mL) | |
| Clotting Agents | |
| Thrombin (Human) | 2.5-6.5 I.U. |
| Buffer Components | |
| Calcium Chloride | 5.88 ± 0.6 mg |
| Sodium Chloride | 3.5-5.5 mg |
| Human Serum Albumin | 45-55 mg |
| Water for Injection | to 1 mL |

Fibrinogen was suspended in a solution with aprotinin, a serine proteinase inhibitor which helps reduce fibrolysis to retain the integrity of the fibrin matrix. This solution was inserted into a first chamber of a two-way syringe (syringe 1). Thrombin was provided separately in a calcium chloride solution in a second chamber of the two-way syringe (syringe 2). Fibrin sealants also contained other components of fibrin scaffolds, such as plasma fibronectin, Factor XIII, plasminogen, and human albumin. TGplPTH$_{1-34}$ was formulated into the fibrinogen component to give a final concentration in the matrix of 0.1 mg/mL to 10 mg/mL in the matrix.

When the fibrinogen and thrombin components were mixed in equal volumes, a clotting process occurred to form fibrin, a natural extracellular matrix. During the gelation process TGplPTH$_{1-34}$ became crosslinked to the matrix. The clotting process took place over 45-60 seconds which allowed for the simultaneous injection of liquids, through a mixer tip, into the defect, where the gel solidified.

Example 4

Treatment of Subchondral Cystic Lesions in Horses Using PTH$_{1-34}$ Cross-Linked to an Injectable Fibrin Matrix Subchondral bone cysts in horses are a similar clinical entity to unicameral bone cysts in humans and have therefore been used as a model to asses the healing potential of PTH$_{1-34}$ cross-linked to fibrin matrices.

12 horses (12 cysts) were subject to surgery whereby the cyst content was removed by drainage curettage. Cysts were located at various joints in the foreleg as well as in the hind leg.

The composition of Example 3 containing equal volumes of fibrinogen and thrombin were injected into the SCLs together with TGplPTH$_{1-34}$ at final concentrations of 10, 1 and 0.4 mg/mL and allowed to polymerize in situ. An average volume of 2 mL of supplemented matrix was used to fill the defects, with volumes ranging from 0.2-5 mL of supplemented matrix. The age of the horses was ranging from 2 months to 11 years. Follow-ups were performed at 2, 4, 6 and 12 months postoperatively investigating radiographic as well as clinical healing.

Intralesional administration resulted in very good healing of the SCLs. All horses analyzed, showed significant progress in clinical and radiographic healing. Radiographic healing was reflected by a higher density of the cyst content and a reduction in cysts size and occurred 2-6 months postoperatively with a tendency to faster healing at lower concentrations of PTH$_{1-34}$. Almost all horses were clinically healed after only 2-4 months postoperatively, and thus showing no lameness anymore.

These results are especially encouraging as successful healing was achieved in adult horses with an age of 3 years or older, known to carry a particularly bad prognosis for bone regeneration.

Concentrations of 0.4 to 10 mg/mL have shown to be effective with a tendency of better healing at lower concentrations.

Treatments with the supplemented matrix containing lower doses of TGplPTH$_{1-34}$ (0.1 mg/mL) have also shown to promote healing of SCLs.

TABLE 3

General patient information and location of the SCL

| Internal No. | Race | Sex | Age | Location of the SCL |
| --- | --- | --- | --- | --- |
| 1 | Inländer | mare | 1 yr | 1st phalanx/ pastern joint, front left |
| 2 | Inländer | mare | 10 yr | cannon bone/ fetlock joint, front right |
| 3 | Württemberger | mare | 11 yr | radius, right |
| 5 | Pinto | mare | 3 yr | patella/ stifle joint, right |
| 7 | Vollblut | mare | 3 yr | sesamoid bone/ fetlock joint, front right |
| 12 | Oldenburger | mare | 3 yr | sesamoid bone/ fetlock joint, front left |
| 13 | Inländer | mare | 3 yr | femur/ stifle joint, right |
| 15 | Inländer | mare | 2 mo | osteomyelitis femur/ stifle joint, right |
| 16 | Inländer | gelding | 2 mo | osteomyelitis femur/ stifle joint, right |
| 18 | Araber | gelding | 5 yr | cannon bone/ fetlock joint, front left |

TABLE 3-continued

General patient information and location of the SCL

| Internal No. | Race | Sex | Age | Location of the SCL |
|---|---|---|---|---|
| 19 | Inländer | stallion | 3 yr | cannon bone/fetlock joint, front right |
| 20 | Inländer | gelding | 9 yr | calcaneus bone, hock joint, right |

TABLE 4

Lameness Grade Before and During Treatment

| | $TGplPTH_{1-34}$ in fibrin matrix [mg/mL] | Clinical healing (lameness grade) | | | | |
|---|---|---|---|---|---|---|
| Internal No. | | Before treatment | 2 months | 4 months | 6 months | 12 months |
| 2 | 10 | 3 | 2 | healed | healed | healed |
| 1 | 1 | 3-4 | 1 | healed | — | healed |
| 3 | 1 | 2 | healed | healed | — | — |
| 5 | 1 | 3 | healed | — | healed | |
| 7 | 1 | 2 | 1 | healed | — | |
| 19 | 1 | 1 | healed | healed | | |
| 12 | 0.4 | 3 | healed | healed | — | |
| 13 | 0.4 | 2 | healed | — | | |
| 15 | 0.4 | 5 | 2 | — | healed | |
| 16 | 0.4 | 4 | 1 | | | |
| 18 | 0.4 | 1 | healed | | | |
| 20 | 0.4 | 3 | — | 1 | | | healed = no lameness present
— = no control visit

The lameness was graded using the criteria set forth in Table 5.

TABLE 5

Lameness Grades and Corresponding Criteria

| Lameness grade | Criteria |
|---|---|
| 1 - minor, unclear | Lameness not consistently apparent: no lameness by walking, only irregular by trotting |
| 2 - minor, clear | Lameness consistently apparent under special circumstances: no lameness by walking, lameness at each step by trotting |
| 3 - medium | Lameness consistently apparent: clear lameness by walking and trotting |
| 4 - high-grade lameness | Severe lameness |
| 5 - highest-grade lameness | no loading anymore |

Example 5

Rabbit Trabecular Bone Model

In order to study the potential for fibrin-$TGplPTH_{1-34}$ to induce the intraosseous thickening of trabecular bone a rabbit model was established. 150 μl of several doses of $TGplPTH_{1-34}$ in fibrin was injected into the distal femurs of sixteen New Zealand White rabbits. The rabbits were anaesthetised and the femoral condyles exposed. A small hole was drilled through the cortical bone into the side of the condyle and the material introduced into the bone through a 22G needle connected to a 1 mL syringe. Doses tested were 0, 0.1, 0.4, and 1.0 mg $TGplPTH_{1-34}$/mL of fibrin matrix with the opposite leg of each rabbit being an untreated control. After 8 weeks the animals were sacrificed and the femoral condyles subjected to μCT to assess bone density following treatment. Bone density increased by approximately 10% following treatment with 1 mg $TGplPTH_{1-34}$/mL fibrin matrix.

Example 6

Visualization, Monitoring and Handling Tests of Radioopaque Fibrin Injected Into Ovine Bone In order to visualise the flow of a fibrin matrix within bone under fluoroscopy and X-ray, an iodine-based contrast agent, iohexol was incorporated into fibrin matrix. 600-800 mg of iohexol was dissolved into the thrombin precursor solution to give final concentrations of 300-400 mg/mL iohexol per fibrin matrix. A range of thrombin in the thrombin precursor composition (4-10 U/mL) was tested. The other components of the fibrin matrix were as described in Table 2.

A gelation test showed that higher concentrations of thrombin were required to form the gel. Both components were injected as liquids simultaneously into the sheep vertebrae and distal femur via a dual syringe and a needle placed into the bone and allowed to polymerise in situ. The gel could be clearly visualised using X-ray and fluoroscopy.

Example 7

Pre-Polymerised Fibrin Injected Into Ovine Bone, Visualisation and Handling Tests In order to visualise and test the handling of a pre-polymerised fibrin matrix within bone under fluoroscopy and X-ray, an iodine-based contrast agent, iohexol was incorporated into the gel. 600-800 mg of iohexol was dissolved into the thrombin dilution buffer to give final concentration of 300-400 mg/mL iohexol in fibrin matrix. The thrombin precursor was added to the buffer-iohexol solution at a concentration of 75 U/mL buffer solution. The other components of the fibrin matrix were as described in Table 2.

A gelation test showed that there was a rapid formation of the matrix upon mixing the precursor components comprising the thrombin and fibrinogen components. Both precursor solutions were injected as liquids simultaneously into a third syringe with a screw thread and allowed to fully polymerise. The contrast agent containing matrix was introduced into ovine vertebrae through a large needle placed in the bone. The gel could be clearly visualised using X-ray and fluoroscopy.

We claim:

1. A method of locally treating non-healthy bone areas in a patient, comprising
   locally administering to a site in bone in need of treatment only one bioactive factor,
   wherein the bioactive factor is provided in a formulation comprising a composition capable of forming a matrix at the site,
   wherein the bioactive factor is selected from the group consisting of parathyroid hormone ($PTH_{1-84}$) or a parathyroid hormone (PTH) fragment selected from the group consisting of $PTH_{1-34}$, $PTH_{1-31}$ and $PTH_{1-38}$; and a fusion peptide comprising ($PTH_{1-84}$) or a PTH fragment selected from the group consisting of $PTH_{1-34}$, $PTH_{1-31}$, and $PTH_{1-38}$ in a first domain and a covalently crosslinkable substrate domain in a second domain, and forming a supplemented matrix at the site,
   wherein the bioactive factor is capable of causing bone growth,
   wherein no other bioactive factor capable of causing bone growth is administered in the method, and
   wherein the site is a non-healthy bone area selected from the group consisting of bone areas affected by osteoporosis and bone cysts.

2. The method of claim 1, wherein the bioactive factor is a fusion peptide, and wherein the fusion peptide is covalently linked to the matrix during its formation.

3. The method of claim 1, wherein the fusion peptide further comprises a degradation site between the first and the second domains.

4. The method of claim 1, wherein the bioactive factor is a fusion peptide comprising $PTH_{1-34}$ in the first domain.

5. The method of claim 1, wherein the second domain of the fusion peptide comprises a transglutaminase substrate domain.

6. The method of claim 5, wherein the transglutaminase substrate domain is a Factor XIIIa substrate domain.

7. The method of claim 1, wherein the second domain of the fusion peptide comprises at least one cysteine.

8. The method of claim 1, wherein the bioactive factor is $PTH_{1-34}$.

9. The method of claim 1, wherein the composition capable of forming a matrix comprises fibrinogen, thrombin, and a calcium source.

10. The method of claim 9, wherein the composition capable of forming a matrix further comprises aprotinin and albumin.

11. The method of claim 1, wherein the matrix is formed by a Michael type addition reaction between a first precursor molecule comprising n nucleophilic groups and a second precursor molecule comprising m electrophilic groups, wherein n and m are at least two and the sum n+m is at least five.

12. The method of claim 11, wherein the electrophilic groups are conjugated unsaturated groups and the nucleophilic groups are selected from the group consisting of thiols and amines.

13. The method of claim 12, wherein the precursor components are functionalized polyethyleneglycols, and wherein the matrix is a polyethylene glycol matrix.

14. The method of claim 1, wherein the composition capable of forming a matrix comprises more than one component, and wherein the formulation is provided in a kit in which at least one of the components of the composition capable of forming a matrix is stored separately from the other components of the composition.

15. The method of claim 14, wherein the kit further comprises an enzyme.

16. The method of claim 1, wherein the matrix is suitable for cell in-growth.

17. The method of claim 1, wherein the formulation is injectable.

18. The method of claim 1, wherein the formulation further comprises a contrast agent.

19. The method of claim 18, wherein the contrast agent is an iodine-containing X-ray contrast agent.

20. The method of claim 1, wherein the site is a bone area affected by osteoporosis and wherein the formulation is administered for prophylactic treatment of osteoporosis.

21. The method of claim 20, wherein the formulation comprises an effective amount of the bioactive factor to increase the bone density at the site compared to the site without treatment with the formulation.

22. The method of claim 21, wherein the concentration of the bioactive factor in the formulation ranges from 0.01 and 2 mg bioactive factor/mL of composition capable of forming the matrix.

23. The method of claim 1, wherein the site is a bone area affected by osteoporosis selected from the group consisting of the femoral neck and vertebra.

24. The method of claim 1, wherein the site is a bone area affected by bone cysts.

25. The method of claim 24, wherein the bone cyst is a subchondral cystic lesion (SCL).

26. The method of claim 25, wherein the SCL occurs in one or more joints selected from the group consisting of the pastern joint, fetlock joint, stifle joint, and hock joint.

* * * * *

UNITED STATES PATENT AND TRADEMARK OFFICE
CERTIFICATE OF CORRECTION

| | | |
|---|---|---|
| PATENT NO. | : 8,318,674 B2 | Page 1 of 1 |
| APPLICATION NO. | : 11/326924 | |
| DATED | : November 27, 2012 | |
| INVENTOR(S) | : Schense et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
Twenty-first Day of October, 2014

Michelle K. Lee
*Deputy Director of the United States Patent and Trademark Office*

```
                         SEQUENCE LISTING

<160> NUMBER OF SEQ ID NOS: 22

<210> SEQ ID NO 1
<211> LENGTH: 5
<212> TYPE: PRT
<213> ORGANISM: Homo sapiens

<400> SEQUENCE: 1

Tyr Ile Gly Ser Arg
1               5

<210> SEQ ID NO 2
<211> LENGTH: 8
<212> TYPE: PRT
<213> ORGANISM: Homo sapiens

<400> SEQUENCE: 2

Asn Gln Glu Gln Val Ser Pro Leu
1               5

<210> SEQ ID NO 3
<211> LENGTH: 5
<212> TYPE: PRT
<213> ORGANISM: Homo sapiens

<400> SEQUENCE: 3

Leu Arg Gly Asp Asn
1               5

<210> SEQ ID NO 4
<211> LENGTH: 5
<212> TYPE: PRT
<213> ORGANISM: Homo sapiens

<400> SEQUENCE: 4

Pro Asp Gly Ser Arg
1               5

<210> SEQ ID NO 5
<211> LENGTH: 5
<212> TYPE: PRT
<213> ORGANISM: Homo sapiens

<400> SEQUENCE: 5

Ile Lys Val Ala Val
1               5

<210> SEQ ID NO 6
<211> LENGTH: 10
<212> TYPE: PRT
<213> ORGANISM: Homo sapiens

<400> SEQUENCE: 6

Arg Asn Ile Ala Glu Ile Ile Lys Asp Ile
1               5                   10

<210> SEQ ID NO 7
<211> LENGTH: 13
```

```
<212> TYPE: PRT
<213> ORGANISM: Homo sapiens

<400> SEQUENCE: 7

Gly Cys Arg Pro Gln Gly Ile Trp Gly Gln Asp Arg Cys
1               5                   10

<210> SEQ ID NO 8
<211> LENGTH: 5
<212> TYPE: PRT
<213> ORGANISM: Homo sapiens

<400> SEQUENCE: 8

Gly Ala Lys Asp Val
1               5

<210> SEQ ID NO 9
<211> LENGTH: 4
<212> TYPE: PRT
<213> ORGANISM: Homo sapiens

<400> SEQUENCE: 9

Lys Lys Lys Lys
1

<210> SEQ ID NO 10
<211> LENGTH: 16
<212> TYPE: PRT
<213> ORGANISM: Homo sapiens

<400> SEQUENCE: 10

Tyr Arg Gly Asp Thr Ile Gly Glu Gly Gln Gln His His Leu Gly Gly
1               5                   10                  15

<210> SEQ ID NO 11
<211> LENGTH: 6
<212> TYPE: PRT
<213> ORGANISM: Homo spaiens

<400> SEQUENCE: 11

Leu Ile Lys Met Lys Pro
1               5

<210> SEQ ID NO 12
<211> LENGTH: 6
<212> TYPE: PRT
<213> ORGANISM: Homo sapiens

<400> SEQUENCE: 12

Asn Phe Lys Ser Gln Leu
1               5

<210> SEQ ID NO 13
<211> LENGTH: 8
<212> TYPE: PRT
<213> ORGANISM: Homo sapiens
<220> FEATURE:
<221> NAME/KEY: Acetylated
<222> LOCATION: (1)..(1)

<400> SEQUENCE: 13

Gly Pro Leu Ala Leu Thr Ala Leu
1               5

<210> SEQ ID NO 14
<211> LENGTH: 6
```

```
<212> TYPE: PRT
<213> ORGANISM: Homo sapiens
<220> FEATURE:
<221> NAME/KEY: Acetylated
<222> LOCATION: (1)..(1)

<400> SEQUENCE: 14

Pro Phe Glu Leu Arg Ala
1               5

<210> SEQ ID NO 15
<211> LENGTH: 5
<212> TYPE: PRT
<213> ORGANISM: Homo sapines

<400> SEQUENCE: 15

Glx Ala Ala Phe Ala
1               5

<210> SEQ ID NO 16
<211> LENGTH: 8
<212> TYPE: PRT
<213> ORGANISM: Homo sapiens

<400> SEQUENCE: 16

Gly Pro Leu Gly Ile Ala Gly Pro
1               5

<210> SEQ ID NO 17
<211> LENGTH: 8
<212> TYPE: PRT
<213> ORGANISM: Homo sapiens

<400> SEQUENCE: 17

Pro His Tyr Gly Arg Ser Gly Gly
1               5

<210> SEQ ID NO 18
<211> LENGTH: 9
<212> TYPE: PRT
<213> ORGANISM: Homo sapiens

<400> SEQUENCE: 18

Pro Gly Ser Gly Arg Ser Ala Ser Gly
1               5

<210> SEQ ID NO 19
<211> LENGTH: 4
<212> TYPE: PRT
<213> ORGANISM: Homo sapiens

<400> SEQUENCE: 19

Tyr Lys Asn Arg
1

<210> SEQ ID NO 20
<211> LENGTH: 46
<212> TYPE: PRT
<213> ORGANISM: Artificial sequence
<220> FEATURE:
<223> OTHER INFORMATION: Modified Parathyroid hormone (PHT), comprisig
      amino acids 1-34 of native PTH as well as a transglutaminase
      substrate domain and a plasmin-degradable sequence

<400> SEQUENCE: 20

Asn Gln Glu Gln Val Ser Pro Leu Tyr Lys Asn Arg Ser Val Ser Glu
1               5                   10                  15
```

```
Ile Gln Leu Met His Asn Leu Gly Lys His Leu Asn Ser Met Glu Arg
                20                  25                  30

Val Glu Trp Leu Arg Lys Lys Leu Gln Asp Val His Asn Phe
            35                  40                  45

<210> SEQ ID NO 21
<211> LENGTH: 42
<212> TYPE: PRT
<213> ORGANISM: Artificial sequence
<220> FEATURE:
<223> OTHER INFORMATION: Modified Parathyroid hormone (PHT), comprisig
      amino acids 1-34 of native PTH as well as a transglutaminase
      substrate domain

<400> SEQUENCE: 21

Asn Gln Glu Gln Val Ser Pro Leu Ser Val Ser Glu Ile Gln Leu Met
1               5                   10                  15

His Asn Leu Gly Lys His Leu Asn Ser Met Glu Arg Val Glu Trp Leu
            20                  25                  30

Arg Lys Lys Leu Gln Asp Val His Asn Phe
            35                  40

<210> SEQ ID NO 22
<211> LENGTH: 21
<212> TYPE: PRT
<213> ORGANISM: Artificial sequence
<220> FEATURE:
<223> OTHER INFORMATION: Fusion protein comprising amino acids 283-396
      of native Parathyroid hormone and a Transglutaminase substrate
      domain

<400> SEQUENCE: 22

Met Asn Gln Glu Gln Val Ser Pro Leu Pro Val Glu Leu Pro Leu Ile
1               5                   10                  15

Lys Met Lys Pro His
            20
```